United States Patent [19]

Muraoka et al.

[11] Patent Number: 4,680,307

[45] Date of Patent: Jul. 14, 1987

[54] CARBACYCLIN ANALOGS

[75] Inventors: Masami Muraoka, Toyonaka; Toshio Nakamura, Nishinomiya; Akihiko Sugie, Toyonaka; Keiichi Ono, Osaka; Michihiro Yamamoto, Nishinomiya, all of Japan

[73] Assignee: Sumitomo Chemical Company, Limited, Osaka, Japan

[21] Appl. No.: 574,125

[22] Filed: Jan. 26, 1984

[30] Foreign Application Priority Data

Feb. 1, 1983 [JP] Japan .................. 58-15837

[51] Int. Cl.$^4$ .............. C07C 59/62; C07C 69/734; C07C 69/78; C07D 315/00; A61K 31/185; A61K 31/215; A61K 31/235; A61K 31/35
[52] U.S. Cl. .................. 514/460; 548/341; 548/509; 548/540; 548/551; 549/79; 549/415; 549/423; 549/464; 549/469; 549/473; 560/56; 560/107; 560/116; 560/117; 560/119; 562/466; 562/498; 562/499; 562/501; 564/172; 564/188; 514/234; 514/277; 514/319; 514/415; 514/423; 514/424; 514/438; 514/459; 514/469; 514/473; 514/510; 514/557; 514/569; 514/572; 514/573; 514/622; 514/623; 544/171; 546/206; 546/342
[58] Field of Search .............. 562/501, 499, 466, 498; 424/317; 560/116, 117, 56, 107; 514/557, 510, 925, 510, 569, 460, 473; 549/421, 475, 415, 473

[56] References Cited

U.S. PATENT DOCUMENTS

| | | | |
|---|---|---|---|
| 4,322,435 | 3/1982 | Kojima et al. .................. | 562/501 |
| 4,423,067 | 12/1983 | Skuballa et al. .................. | 424/317 |
| 4,479,966 | 10/1984 | Hayashi et al. .................. | 560/116 |
| 4,493,846 | 1/1985 | Ono et al. .................. | 562/501 X |

FOREIGN PATENT DOCUMENTS

| | | | |
|---|---|---|---|
| 0036730 | 9/1981 | European Pat. Off. . | |
| 0057660 | 8/1982 | European Pat. Off. .............. | 562/501 |
| 0110539 | 7/1983 | Japan .................. | 562/501 |
| 0013747 | 1/1984 | Japan .................. | 562/501 |
| 0016852 | 1/1984 | Japan .................. | 562/501 |
| 2017699 | 10/1979 | United Kingdom . | |

OTHER PUBLICATIONS

Derwent Abstract, No. 18487 D/11, abstract of Japanese Kokai 56-5456.
Journal of Pharmacology and Experimental Therapeutics, vol. 206, No. 1, 1978, pp. 132-138, Crane et al.

Primary Examiner—Michael L. Shippen
Assistant Examiner—Patricia M. Scott
Attorney, Agent, or Firm—Stevens, Davis, Miller & Mosher

[57] ABSTRACT

A compound of the formula:

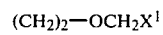
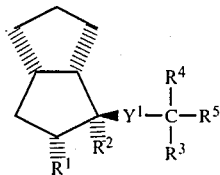

wherein $X^1$ is a free or an esterified carboxyl group, or a group of the formula:

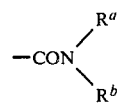

($R^a$ and $R^b$ are each independently a hydrogen atom, a $C_1$-$C_4$ alkyl group, a $C_3$-$C_7$ cycloalkyl group, a benzyl group, a phenyl group, a phenyl group substituted with a halogen atom or a $C_1$-$C_4$ alkyl group, or, when taken together with the adjacent nitrogen atom to which they are attached, they represent a 5 to 7 membered saturated heterocyclic group, $Y^1$ is a group of the formula:

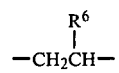

($R^6$ is a hydrogen atom or $C_1$-$C_4$ alkyl group),

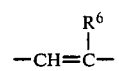

($R^6$ is as defined above),

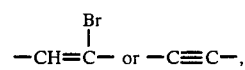

$R^1$ is a hydrogen atom, a hydroxyl group or a protected hydroxyl group, $R^2$ is a hydrogen atom or $R^1$ and $R^2$, when taken together, mean a shingle linkage to from a double bond between the carbon atoms which they are linked, $R^3$ is a hydroxyl group or a protected hydroxyl group, $R^4$ is a hydrogen atom or a $C_1$-$C_4$ alkyl group, $R^5$ is a hydrogen atom, a $C_1$-$C_{12}$ alkyl group, a $C_2$-$C_{12}$ alkenyl group, a $C_2$-$C_{12}$ alkynyl group, a $C_3$-$C_{10}$ cycloalkyl group, a $C_4$-$C_{10}$ cycloalkenyl group, a hydroxy $C_1$-$C_{12}$ alkyl group, a $C_3$-$C_{10}$ heterocyclic group, a phenyl group optionally substituted with a halogen atom; a hydroxyl group, a $C_1$-$C_4$ alkyl group, a trifluoromethyl group, or a $C_1$-$C_4$ alkyl group or a formula: A-B (A is a $C_1$-$C_7$ alkylene chain and B is a $C_3$-$C_{10}$ cycloalkyl group, a $C_4$-$C_{10}$ cycloalkenyl group, a $C_1$-$C_{12}$ alkoxy group, a $C_3$-$C_{10}$ cycloalkoxy group, a $C_4$-$C_{10}$ cycloalkenyloxy group, a $C_3$-$C_{10}$ heterocyclic group, or a phenyl or phenoxy group optionally substituted with a halogen atom, a hydroxy group, a $C_1$-$C_4$ alkyl group, a trifluoromethyl group or a $C_1$-$C_4$ alkoxy group); or a non-toxic pharmaceutically acceptable salt thereof. Said compound have strong anti-ulcerous action or antithrombotic action, and are useful in treatment of ulcer or thrombosis.

43 Claims, No Drawings

CARBACYCLIN ANALOGS

The present invention relates to novel bicyclooctane compounds, their production and use.

More particularly, this invention relates to novel bicyclooctane compounds, to a pharmaceutical composition containing at least one of the bicylooctane compounds and to a process for production thereof.

The novel bicyclooctane compounds provided by the present invention are those represented by the formula:

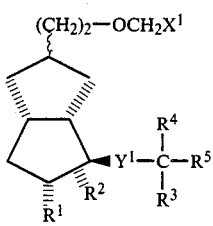

wherein $X^1$ is a free or an esterified carboxyl group, or a group of the formula:

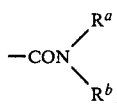

($R^a$ and $R^b$ are each independently a hydrogen atom, a $C_1$-$C_4$ alkyl group, a $C_3$-$C_7$ cycloalkyl group, a benzyl group, a phenyl group, a phenyl group substituted with a halogen atom or a $C_1$-$C_4$ alkyl group, or, when taken together with the adjacent nitrogen atom to which they are attached, they represent a 5 to 7 membered saturated heterocyclic group), $Y^1$ is a group of the formula:

$$-CH_2\overset{R^6}{\underset{|}{C}}H-$$

($R^6$ is a hydrogen atom or $C_1$-$C_4$ alkyl group),

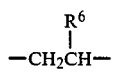

($R^6$ is as defined above),

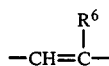

$R^1$ is a hydrogen atom, a hydroxyl group or a protected hydroxyl group, $R^2$ is a hydrogen atom or $R^1$ and $R^2$, when taken together, mean a single linkage to form a double bond between the carbon atoms which they are linked, $R^3$ is a hydroxyl group or a protected hydroxyl group, $R^4$ is a hydrogen atom or a $C_1$-$C_4$ alkyl group, $R^5$ is a hydrogen atom, a $C_1$-$C_{12}$ alkyl group, a $C_2$-$C_{12}$ alkenyl group, a $C_2$-$C_{12}$ alkynyl group, a $C_3$-$C_{10}$ cycloalkyl group, a $C_4$-$C_{10}$ cycloalkenyl group, a hydroxy $C_1$-$C_{12}$ alkyl group, a $C_3$-$C_{10}$ heterocyclic group, a phenyl group optionally substituted with a halogen atom, a hydroxyl group, a $C_1$-$C_4$ alkyl group, a trifluoromethyl group, or a $C_1$-$C_4$ alkoxy group or a formula: A-B (A is a $C_1$-$C_7$ alkylene chain and B is a $C_3$-$C_{10}$ cycloalkyl group, a $C_4$-$C_{10}$ cycloalkenyl group, a $C_1$-$C_{12}$ alkoxy group, a $C_3$-$C_{10}$ cycloalkoxy group, a $C_4$-$C_{10}$ cycloalkenyloxy group, a $C_3$-$C_{10}$ heterocyclic group, or a phenyl or phenoxy group optionally substituted with a halogen atom, a hydroxy group, a $C_1$-$C_4$ alkyl group, a trifluoromethyl group or a $C_1$-$C_4$ alkoxy group).

Some typical compounds of the invention are represented by the formulae:

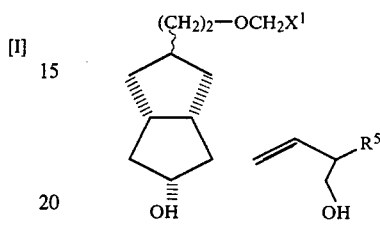

wherein $X^1$ and $R^5$ are each as defined above; or:

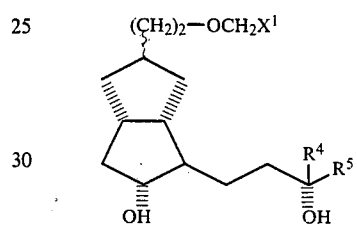

wherein $X^1$, $R^4$ and $R^5$ are each as defined above; or:

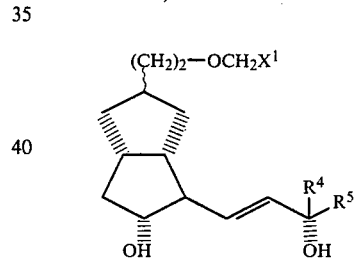

wherein $X^1$, $R^4$ and $R^5$ are each is defined above.

Other typical compounds represented by formula I include substituents wherein $X^1$ is a free carboxyl group, a $C_1$-$C_4$ alkoxycarbonyl group, or a group of the formula:

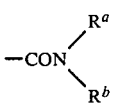

($R^a$ and $R^b$ are each independently a hydrogen atom, a $C_1$-$C_4$ alkyl group, a benzyl group or a phenyl group), $R^5$ is a $C_1$-$C_{12}$ alkyl group, a $C_2$-$C_{12}$ alkenyl group, a $C_2$-$C_{12}$ alkynyl group, a $C_3$-$C_{10}$ cycloalkyl group, a $C_4$-$C_{10}$ cycloalkenyl group, a phenyl group optionally substituted with a halogen atom or a formula: A-B (A is a methylene group or a ethylene group and B is a $C_3$-$C_{10}$ cycloalkyl group, a $C_4$-$C_{10}$ cycloakenyl group, a $C_1$-$C_{12}$ alkoxy group, a $C_3$-$C_{10}$ cycloalkoxy group, or a phenoxy group optionally substituted with a halogen atom).

Further compounds according to the invention comprise any of the above general formulae, wherein the esterified carboxyl group is a $C_1$–$C_4$ alkoxycarbonyl group, an aryloxycarbonyl group, an aralkyloxycarbonyl group, a ($C_1$–$C_4$ alkoxy)methoxycarbonyl group, a ($C_2$–$C_5$ alkanoyloxy)carbonyl group, a ($C_3$–$C_7$ cycloalkyloxy)carbonyl group, an arylcarbonylmethoxycarbonyl group or a (hydroxy $C_1$–$C_4$ alkoxy)carbonyl group; and wherein $X^1$ is a free carboxyl group, a $C_1$–$C_4$ alkoxycarbonyl group, or a group of the formula:

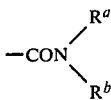

($R^a$ and $R^b$ are each independently a hydrogen atom, a $C_1$–$C_4$ alkyl group, a benzyl group or a phenyl group); or wherein $X^1$ is a free carboxyl group, a $C_1$–$C_4$ alkoxycarbonyl group, or a group of the formula:

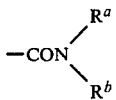

($R^a$ and $R^b$ are each independently a hydrogen atom, a $C_1$–$C_4$ alkyl group, a benzyl group or a phenyl group), $R^5$ is a $C_1$–$C_{12}$ alkyl group, a $C_2$–$C_{12}$ alkenyl group, a $C_2$–$C_{12}$ alkynyl group, or a $C_3$–$C_{10}$ cycloakyl group; or wherein $X^1$ is a free carbonxyl group, a $C_1$–$C_4$ alkoxycarbonyl group, or a group of the formula:

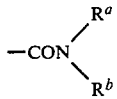

($R^a$ and $R^b$ are each independently a hydrogen atom, a $C_1$–$C_4$ alkyl group, a benzyl group or a phenyl group), $R^4$ is a hydrogen atom, $R^5$ is a $C_1$–$C_{12}$ alkyl group, or a $C_3$–$C_{10}$ cycloalkyl group; or wherein $X^1$ is a free carboxyl group, a $C_1$–$C_4$ alkoxycarbonyl group, or a group of the formula:

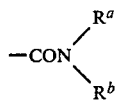

($R^a$ and $R^b$ are each independently a hydrogen atom, a $C_1$–$C_4$ alkyl group, a benzyl group, or a phenyl group), $R^4$ is a hydrogen atom or a methyl group, $R^5$ is a $C_1$–$C_{12}$ alkyl group, a $C_2$–$C_{12}$ alkenyl group, a $C_2$–$C_{12}$ alkynyl group, a $C_3$–$C_{10}$ cycloakyl group, a $C_4$–$C_{10}$ cycloalkenyl group, a phenyl group optionally substituted with a halogen atom or a formula: A–B (A is a methylene group or a ethylene group and B is a $C_3$–$C_{10}$ cycloalkyl group, a $C_4$–$C_{10}$ cycloalkenyl group, a $C_1$–$C_{12}$ alkoxy group, a $C_3$–$C_{10}$ cycloalkoxy group, or a phenoxy group optionally substituted with a halogen atom).

In the significances as used above, the term "halogen" includes fluorine, chlorine, bromine and iodine; the terms "$C_1$–$C_4$ alkyl" and "$C_1$–$C_4$ alkoxy" are each meant straight or branched chain alkyl and alkoxy group having from 1 to 4 carbon atoms (e.g. methyl, ethyl, n-propyl, isopropyl, n-butyl, methoxy, ethoxy, n-propoxy, isopropoxy, n-butoxy, etc.).

The term "$C_1$–$C_{12}$ alkyl" in the both cases, "$C_1$–$C_{12}$ alkyl" and "$C_1$–$C_{12}$ alkyl in the $C_1$–$C_{12}$ alkoxy group" is meant a straight or branched chain alkyl group having from one to 12 carbon atoms (e.g. methyl, ethyl, n-propyl, isopropyl, n-butyl, isobutyl, n-pentyl, isopentyl, 1-methylpentyl, 2-methylpentyl, 1,1-dimethylpentyl, 1-ethylpentyl, 2-ethylpentyl, n-hexyl, 1-methylhexyl, 2-methylhexyl, 3-methylhexyl, heptyl, 1-methylheptyl, 2-methylheptyl, 1-ethylheptyl, 2-ethylheptyl, n-octyl, 1-methyloctyl, 2-methyloctyl, 1-ethyloctyl, 2-ethyloctyl, 2,6-dimethylheptyl 1,6-dimethylheptyl, n-nonyl, 1-methylnonyl, 2-methylnonyl, n-decyl, 1-methyldecyl, 2-methyldecyl, 2-ethyldecyl etc.).

The terms "$C_2$–$C_{12}$ alkenyl" and "$C_2$–$C_{12}$ alkynl" are meant straight or branched chain alkenyl group or alkynyl group having from 2 to 12 carbon atoms (e.g. vinyl, 2-propenyl, 2-butenyl, 2-pentenyl, 2-hexenyl, 5-heptenyl, 6-methyl-5-heptenyl, 2,6-dimethyl-5-heptenyl, 3-pentenyl, 4-pentenyl, 2,6-dimethyl-5-octenyl, 1,1,6-trimethyl-5-heptenyl, 4,8-dimethyl-7-nonenyl, 2,6-dimethyl-1,5-heptadienyl, 2-propynyl, 1-methylenepentyl, 2-butynyl, 2-pentynyl, 3-pentynyl, 1-methyl-3-pentynyl, 4-pentynyl, 4-hexynyl, 5-heptynyl, 6-heptynyl, 2-methyl-5-heptynyl, etc.).

The term "$C_3$–$C_{10}$ cycloalkyl" in the both cases, "$C_3$–$C_{10}$ cycloalkyl" and "$C_3$–$C_{10}$ cycloalkyl in the $C_3$–$C_{10}$ cycloalkoxy group" is meant cyclic alkyl group which is optionally substituted with $C_1$–$C_4$ alkyl group or alkenyl group and which has from 3 to 10 carbon atoms (e.g. cyclopropyl, cyclobutyl, cyclopentyl, cyclohexyl, cycloheptyl, 2-isopropylidenemethyl-3,3-dimethylcyclopropyl, 2-propylcyclopropyl, 3-ethylcyclobutyl, 3-ethylcyclopentyl, 4-methylcyclohexyl, 3-ethylcyclohexyl, 4-methylcyclo-heptyl, 2-isopropyl-5-methylcyclohexyl, norbornyl, adamantyl etc.).

The term "$C_4$–$C_{10}$ cycloalkenyl" in the both cases, "$C_4$–$C_{10}$ cycloalkenyl" and "$C_4$–$C_{10}$ cycloalkenyl in the $C_4$–$C_{10}$ cycloalkenyloxy" is meant cyclic alkenyl group having from 4 to 10 carbon atoms (e.g. bicyclo[4,3,0]-nona-3-en-8-yl, 3-cyclopentenyl, 3-cyclohexenyl, 3-cyclohexenyl, tetrahydro-2-indanyl etc.).

The term "hydroxy $C_1$–$C_{12}$ alkyl" is meant straight or branched alkyl group which has from one to 12 carbon atoms and is substituted with hydroxyl group (e.g. hydroxymethyl, 2-hydroxyethyl, 3-hydroxypropyl, 4-hydroxybutyl, 5-hydroxypentyl, 6-hydroxyhexyl, 7-hydroryheptyl, 8-hydroxyoctyl, 10-hydtoxydecyl, 5-hydroxyhexyl, 4-hydroxypentyl, 5-hydroxy-1,1-dimethylpentyl, 5-hydroxy-2-methylpentyl, 5-hydroxy-1-methylpentyl, 6-hydroxy-2-methylhexyl etc.).

The term "$C_3$–$C_{10}$ heterocyclic group" is meant mono or dicyclic group having from 3 to 10 carbon atoms and at least one of hetero atoms selected from nitrogen atoms, sulfur atoms, and oxygen atoms (e.g. piperidine, morpholine, pyrrolidine, piperazine, tetrahydrofuran, tetrahydrothiophene, furan, thiophene, imidazole, pyridine, oxazole, isooxazole, pyrrole, pyrazole, pyrimidine, indole, benzofuran, purine, benzothiophene, quinoline, pyrro-lidone, dihydrothiophene, dihydrobenzofuran, 1,4-benzodioxane, etc.).

The term "$C_1$–$C_7$ alkylene" is meant straight or branched alkylene chain having from one to 7 carbon atoms (e.g. methylene, ethylene, trimethylene, tetramethylene, pentamethylene, hexamethylene, heptamethylene, methylmethylene, dimethylmethylene, 1,1-dimethylethylene, 2-methyltetramethylene, 1-methylpentamethylene, 2-methylhexamethylene, 1-ethylethylene, 2-ethylethylene, 2-ethyltrimethylene, etc.).

The term "5 to 7 membered saturated heterocyclic group" includes piperidine, morpholine, pyrrolidine, homopiperidine, piperazine, N-($C_1$-$C_4$) alkylpiperazine, etc.).

The term "$C_3$-$C_7$ cycloalkyl" is meant a cyclic alkyl group which is optionally substituted with a $C_1$-$C_4$ alkyl group and has from 3 to 7 carbon atoms (e.g. cyclopropyl, cyclobutyl, cyclopentyl, cyclohexyl, cycloheptyl, 3-ethylcyclopentyl, 4-methylcyclohexyl, etc.).

The term "esterified carboxyl group" includes $C_1$-$C_4$ alkoxycarbonyl, aryloxycarbonyl (e.g. phenoxycarbonyl, naphthoxycarbonyl), aralkyloxycarbonyl (e.g. benzyloxycarbonyl, phenethyloxycarbonyl), ($C_1$-$C_4$ alkoxy)methoxycarbonyl, ($C_2$-$C_5$ alkanoyloxy)methoxycarbonyl (e.g. acetoxymethoxycarbonyl), ($C_3$-$C_7$ cycloalkyloxy)carbonyl, arylcarbonylmethoxycarbonyl and (hydroxy $C_1$-$C_4$ alkoxy)carbonyl.

The term "protected hydroxy group" is meant a hydroxy group protected with $C_1$-$C_4$ alkanoyl (e.g. acetyl, propionyl), benzoyl, substituted benzoyl, tetrahydropyranyl, tetrahydrofuryl or ($C_1$-$C_4$ alkoxy)methyl.

A tremendous amount of research in synthetic organic chemistry, pharmacology and clinical medicine of prostaglandins has been performed since discovery of prostaglandins.

In 1976, J. Vane of Wellcome foundation reported isolation and biological effects of prostacyclin [prostaglandin $I_2$]. [S. Moncada, R. Gryglewski, S. Bunting, and J. R. Vane, Nature (London), 263, 663 (1976)].

Prostaglandin $I_2$[II], which is shown below, has several excellent pharmacological activities, for example, hypotensive, vasodilating, antiallergic, antiulcerogenic, antithrombotic, activity, and is expected to be useful in treating asthma, ulcer, thrombosis, or hypertention.

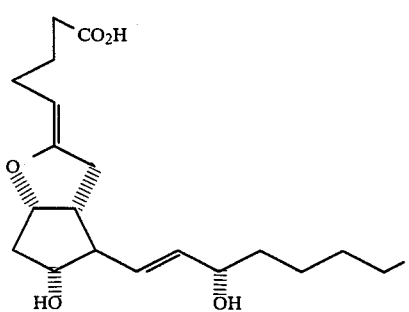

[II]

However, prostaglandin $I_2$ (referred to as "$PGI_2$", hereinafter) may not be used as medicine owing to its instability.

As the result of a study, it has now been found that the novel bicyclooctane compounds [I] of the present invention and their non-toxic pharmaceutically acceptable salts have antithrombotic, antihypertensive action or anti-ulcerous action and are useful in treatment of ulcer, thrombosis or hypertention. Especially, the present compounds [I] are useful as antithrombotic or antiulcerous drugs. In addition, the undesirable instability is absent in the compounds [I] of this invention.

Accordingly, a basic object of the present invention is to provide novel and stable bicyclooctane compounds [I] having excellent pharmacological activity.

Another object of the present inveniton is to provide a process for producing those compounds [I]. Further object of the present invention is to provide a pharmaceutical composition containing a compound of the formula [I]. These and other objects will be apparent to those skilled in the art to which the present invention pertains from the foregoing and subsequent descriptions.

The novel bicyclooctane compound [I] of the invention can be prepared by the following two methods. (1) The bicyclooctane compound of the formula [I]

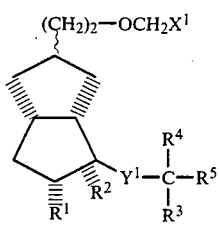

[I]

wherein $X^1$, $Y^1$, $R^1$, $R^2$, $R^3$, $R^4$, and $R^5$ are each as defined above, can be prepared from a carbonyl compound of the formula [III]

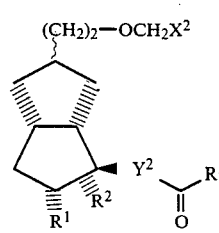

[III]

wherein $X^2$ is a free or esterified carboxyl group, or a group of the formula:

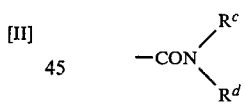

($R^c$ and $R^d$ are each independently a $C_1$-$C_4$ alkyl group, a $C_3$-$C_7$ cycloalkyl group, a benzyl group, a phenyl group, a phenyl group substituted with a $C_1$-$C_4$ alkyl group, or when taken together with the adjacent nitrogen atom to which they are attached, they represent a 5 to 7 membered saturated heterocyclic group), $Y^2$ is a group of the formula:

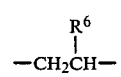

$S(R^6$ is a hydrogen atom or a $C_1$-$C_4$ alkyl group), or

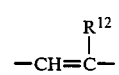

($R^{12}$ is a hydrogen atom, a $C_1$-$C_4$ alkyl group or a bromine atom), $R^1$, $R^2$ and $R^5$ are each as defined above by reacting the latter with a reducing agent or an organometalic-compound of the formula:

$$M-R^7 \quad [IV]$$

wherein $R^7$ is a $C_1-C_4$ alkyl group and M is a lithium atom or —Mg halo (halo is a halogen atom), optionally followed by hydrolysis of an amide group or ester group, esterification of a carboxyl group, amidation of a free or esterified carboxyl group, reduction of a vinylene group, dehydrohalogenation of halogenated vinylene group, protection of hydroxy group and/or deprotection of a protected hydroxyl group.

(2) The bicyclooctane compounds [I] can be also prepared from an alcohol compound of the formula:

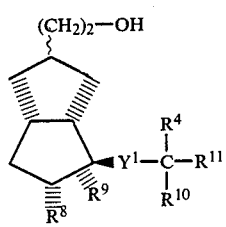

[V]

wherein $R^4$ and $Y^1$ are each as defined above and $R^8$ is a hydrogen atom or a protected hydroxyl group, $R^9$ is a hydrogen atom, or $R^8$ and $R^9$, when taken together, mean a single linkage to form a double bond between the carbon atoms to which they are linked, is a protected hydroxy group and $R^{11}$ is a hydrogen atom, a $C_1-C_{12}$ alkyl group, a $C_2-C_{12}$ alkenyl group, a $C_2-C_{12}$ alkynyl group, a $C_3-C_{10}$ cycloalkyl group, a $C_4-C_{10}$ cycloalkenyl group, a protected hydroxyl $C_{1l}-C_{12}$ alkyl group, a $C_3-C_{10}$ heterocyclic group, a phenyl group optionally substituted with a halogen atom, a protected hydroxyl group, a $C_1-C_4$ alkyl group, a trifluoromethyl group or a $C_1-C_4$ alkoxy group or a formula: A-B'(A is a $C_1-C_7$ alkylene chain and B'is a $C_3-C_{10}$ cycloalkyl group, a $C_4-C_{10}$ cycloalkenyl group, a $C_1-C_{12}$ alkoxy group, a $C_3-C_{10}$ cycloalkoxy group, a $C_4-C_{10}$ cycloalkenyloxy group, a $C_3-C_{10}$ heterocyclic group, or a phenyl or phenoxy group optionally substituted with a halogen atom, a protected hydroxyl group, a $C_1-C_4$ alkyl group, a trifluoromethyl group or a $C_1-C_4$ alkoxy group), by reacting the latter with halogeno compound of the formula:

$$halo-CH_2-X^2 \quad [iv]$$

wherein halo is a halogen atom, optionally followed by hydrolysis of a amido group or ester group, esterification of carboxyl group, reduction of vinylene group, protection of a hydroxyl group and/or deprotection of a protected hydroxyl group.

The sequence of the steps from the carbonyl compound [III] or the alcohol [V] to the bicyclooctane compound [I] as stated above may be represented by the following scheme.

Scheme A

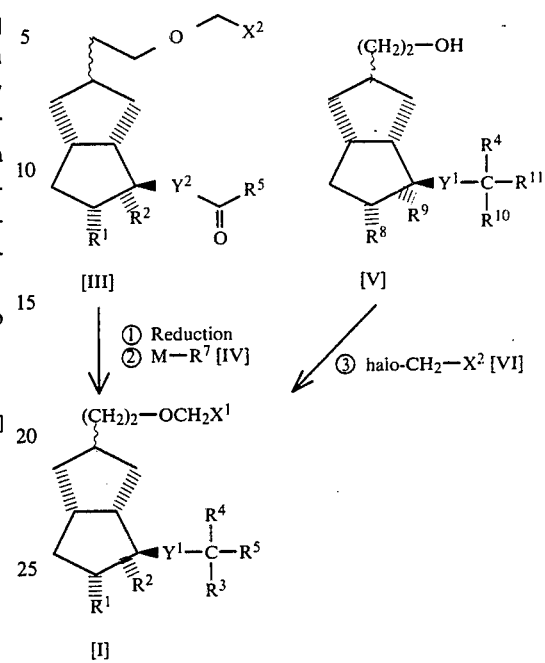

Step 1

Production of the bicyclooctane compound [I] from the carbonyl compound [III] by reduction of a carbonyl group.

The carbonyl compound [III] can be converted into the corresponding alcohol compound by reacting of the former with a reducing agent in an inert solvent (e.g. THF, ether, dimethoxyethane, pentane, hexane, benzene, toluene, metanol, ethanol) at a temperature in the range from $-70°$ C. to room temperature.

As the reducing agent, there may be used for example trialkylborohydride (e.g. lithium triisobutyl borohydride), bis(2,4,6-tri-tert-butylphenoxy)aluminum hydride, sodium borohydride, zinc borohydride, diisobutyl aluminum hydride, diisobutyl aluminum-2,6-di-t-butyl-4-methylphenol, ethoxy 1,1'-binaphthyl-2,2'-dioxyaluminum lithium hydride.

The protection and deprotection of a hydroxyl group can be carried out by conventional procedure [Protective Group in Organic Chemistry, Edited by J. F. W. McOmie (1973) 95-143].

The reduction of a vinylene group can be accomplished by catalytic hydrogenation in an inert solvent (e.g. alkanol, aqueous alkanol) at a temperature in the range from 0° C. to room temperature.

The dehydrohalogenation of halogenated vinylene group can be accomplished by reacting with a strong base (e.g. potassium t-butoxide, sodium methoxide) in an ineart solvent (e.g. t-butanol) at a temperature in the range from 0° C. to room temperature.

Step 2

Reaction of a carbonyl group [III] with an organometalic compound [IV].

The carbonyl compound [III] can be converted into the corresponding alcohol compound by reacting of the former with an organometalic compound [IV] in an inert solvent (e.g. ether, THF, dioxane) at a temperature in the range from −70° C. to room temperature. The organometalic compound [IV] can be prepared by the conventional procedures.

Step 3

The alkylation of the alcohol [V] can be carried out by reacting of [V] with the halogeno compound [VI] in an inert solvent (e.g. benzene, toluene, xylene, DMF, DMSO, alkanol) in the presence of an alkali (e.g. alkali metal hydride, alkali metal amide, alkali metal, alkali metal t-butoxide) at a temperature in the range from room temperature to the boiling temperature of the solvent.

The steps of amidation of a carboxyl group, amidation of a esterified carboxy group, hydrolysis of a amido group into a carboxyl group, hydrolysis of an esterified carboxyl group and esterification of a carboxyl group may be represented by the following scheme:

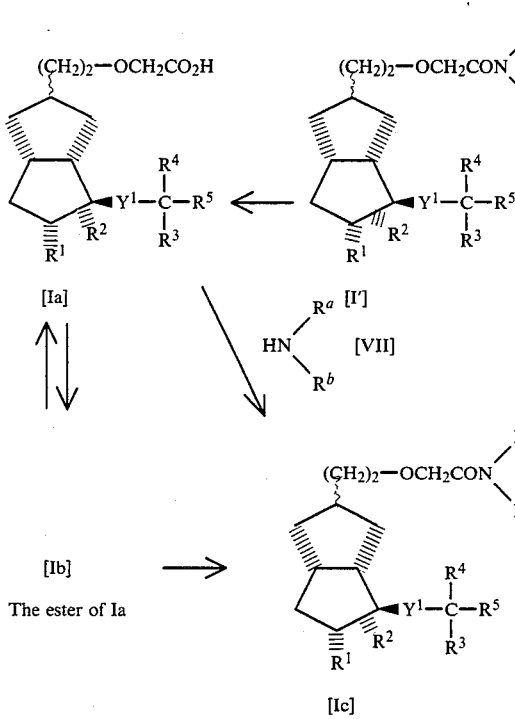

Amidation of a carboxyl group can be carried out by conventional procedure. For instance, it can be accomplished in an inert solvent (e.g. ether, THF) by treating a carboxyl compound [Ia] with an amine [VII] ($R^a$ and $R^b$ are each as defined above) in the presence of dehydrolyzing agent (e.g. dicyclohexylcarbodiimide) at a temperature in the range from 0° C. to room temperature, or by treating the functionally active derivative (e.g. mixed acid anhydride) of [Ia] with the amine [VII] in an inert solvent (e.g. ether, THF, chloroform) at a temperature in the range from −10° C. to room temperature.

Amidation of an esterified carboxyl group can be carried out by treating an ester compound [Ib] with the amine [VII] in an inert solvent (e.g. DMF, methanol, ethanol, THF) at a temperature in the range from room temperature to the boiling temperature of the solvent.

Hydrolysis of a amido group into a carboxyl group can be carried out in the presence of an alkali (e.g. sodium hydroxide, potassium hydroxide) in an inert solvent (e.g. aqueous alkanol, DMSO) at a temperature in the range from 60° C. to the boiling temperature of the solvent.

The hydrolysis of the ester compound [Ib] and the esterification of a carboxyl group can be carried out by conventional procedure.

The carbonyl compound [III] used as an intermediate in the present invention can be prepared from a olefin compound [VIII] by the process shown in the scheme C.

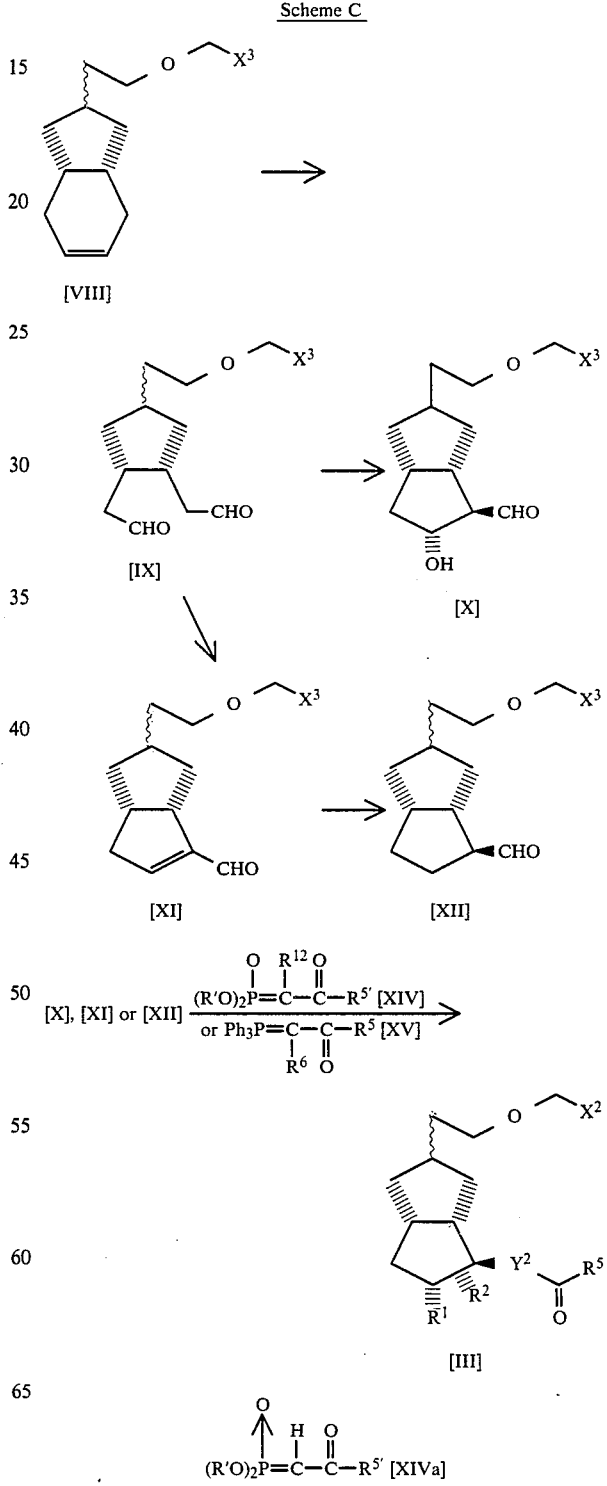

-continued
Scheme C

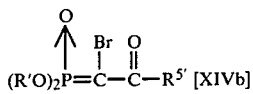

In the formula illustrated in the scheme C, $X^3$ is same as $X^2$ provided that $X^3$ is not a free carboxyl group, R' is a $C_1$–$C_4$ alkyl group, $R^{5\prime}$ is same as $R^5$ provided that $R^{5\prime}$ is not a hydrogen atom, and $R^1$, $R^2$, $R^5$, $R^6$, $R^{12}$, and $Y^2$ are each as defined above.

Detail explanation of Scheme C is as follows:

Oxidation of the compound [VIII] into the dialdehyde [IX] can be accomplished by treating with sodium metaperiodate in the presence of a catalytic amount of osmium tetroxide in an inert solvent at a temperature in the range from 0° C. to room temperature. Example of the inert solvent include water, ethers (e.g. dioxane, THF) and aqueous ethers.

The dialdehyde [IX] can be also obtained by ozonization of the compound [VIII] at a temperature in the range from −80° C. to −30° C., followed by reductive cleavage with dialkyl sulfide, triphenylphosphine, sodium bisulfite, zinc or the like, or by the catalytic hydrognation in the presence of a palladium on charcoal.

Examples of the inert solvent for ozonization include alkanols (methanol, ethanol), halogenated hydrocarbon and ester. Reduction of an ozonide may be accomplished by a per se conventional procedure at a temperature in the range from −30° C. to 0° C.

Aldol condensation of the dialdehyde [IX] into an aldole derivative [X] is carried out in the presence of an acid or a base in an inert solvent (e.g. water, alkanols, aqueous alkanols, ethers, esters) at a temperature in the range from −70° C. to room temperature. Example of the suitable base are alkali hydroxide (e.g. potassium hydroxide, sodium hydroxide), alkali carbonate and alkali hydrogen carbonate.

The compound [XI] can be obtained by treating the dialdehyde [IX] in the presence of an acid or a base in an inert solvent at a temperature in the range from room temperature to the boiling temperature of the solvent.

The compound [XI] can be easily converted into the compound [XII] by conventional catalytic hydrogenation in the presence of a palladium on charcoal, if necessary, followed by epimerization.

The compounds [X, XI, XII] can be each easily converted into a carbonyl compound [III] by reacting of the former with a compound [XIV] or a compound [XV] in an inert solvent (e.g. dioxane, ether, THF, dimethoxyethane, benzene, toluene, n-hexane, DMSO) at a temperature in the range from −10° to 50° C., optionally followed by protection of a hydroxy group, hydrolysis of an ester group and/or reduction of a vinylene group.

The compound [XIVb] which is part of [XIV] can be obtained by reacting of the compound [XIVa] with N-bromosuccineimide in an inert solvent (e.g. THF, dimethoxyethane) at a temperature in the range from −10° C. to room temperature.

The selective reduction of a compound [XIII]

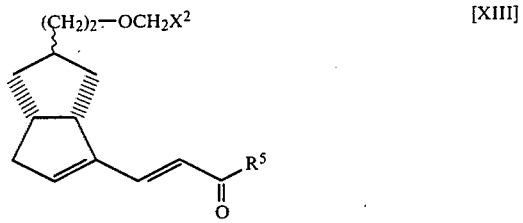

where in $X^2$ and $R^5$ are each as defined above into a compound [XVI]

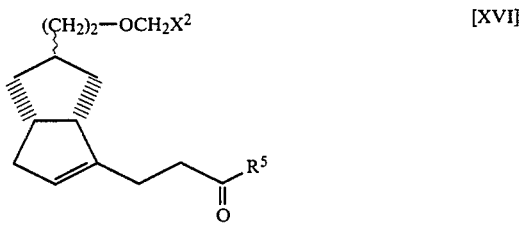

wherein $X^2$ and $R^5$ are each as defined above, can be carried out by reacting the former with trialkylsilane in the presence of titanium tetrachloride in an inert solvent (e.g. halogenated hydrocarbon) at a temperature in the range from −78° to 0° C.

(1) The compound [VIII] can be prepared from an alcohol compound [XVII] by reacting the latter with halogeno compound [VI].

(2) The compound [VIII] can be also prepared from an alcohol compound [XVIII] by oxidation of the latter to the carboxyl compound followed by esterification and/or amidation of a free or esterified carboxyl group. The sequence of the steps from the alcohol compound [XVII] or the compound [XVIII] to the compound [VIII] is represented in the Scheme D.

Scheme D

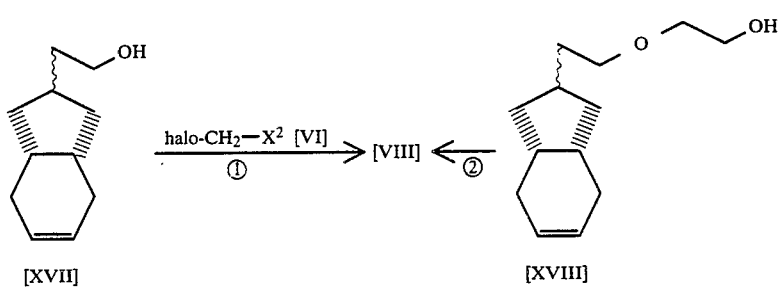

In the formula illustrated in the Scheme D, halo and $X^2$ are each as defined above.

Step 1

Alkylation of the alcohol [XVII] can be carried out by reacting of [XVII] with the halogeno compound

[VI] in an inert solvent (e.g. benzene, toluene, xylene, DMF, DMSO, alkanol) in the presence of an alkali (e.g. alkali metal hydride, alkali metal amide, alkali metal, alkali metal t-butoxide), at a temperature in the range from room temperature to the boiling temperature of the solvent.

Step 2

Oxidation of the alcohol [XVIII] can be carried out by reacting with cromium oxide (e.g. with the solution of cromium oxide in dilute sulfuric acid in acetone at ambient temperature).

Esterification and amidation can be accomplished by the procedure mentioned above.

The alcohol compound [XVII] can be prepared by way of the following three paths shown in the Scheme E, F, and G.

The compound [XVII] can be obtained from the carbonyl compound [XIX] by the process shown in the Scheme E.

Scheme E

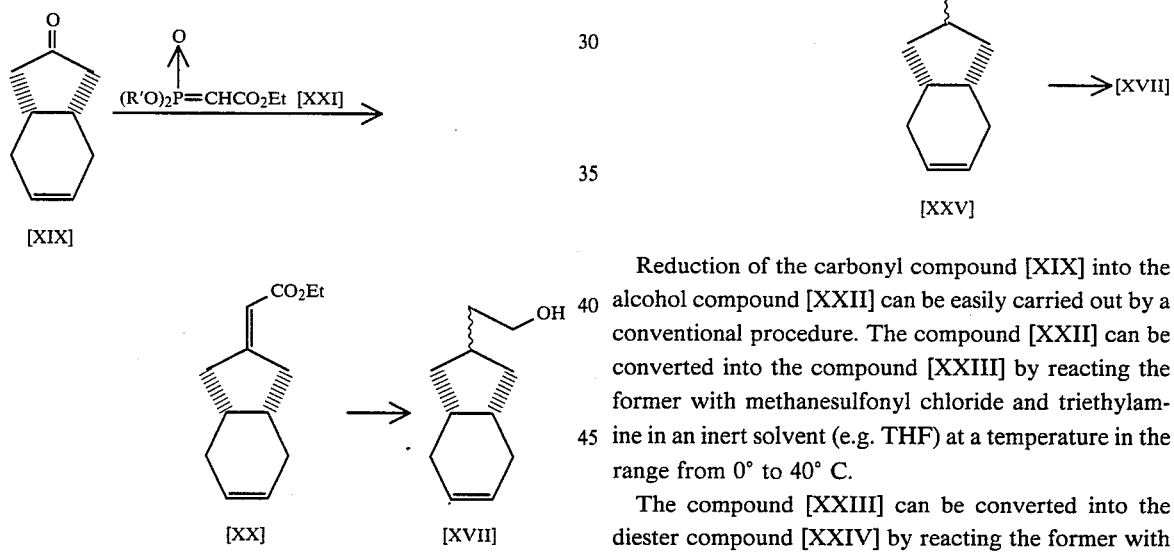

The compound [XIX] can be easily converted into the ester compound [XX] by reacting of the former with a compound [XXI] in an inert solvent (e.g. dioxane, ether, THF, dimethoxyethane, benzene, DMSO) at a temperature in the range from −10° to 50° C. The compound [XX] can be easily converted into the alcohol compound [XVI] by Birch reduction of the former according to the known procedure [J. Org. Chem., (1972)]. The reduction can be accomplished by treating the ester [XX] with lithium or sodium in the presence of liquid ammonia and alcohol (e.g. methanol, ethanol) in an inert solvent (e.g. ether, dioxane) at a temperature in the range from −70° to −40° C. The compound [XVII] can be obtained from the compound [XIX] also by the process shown in the Scheme F.

Scheme F

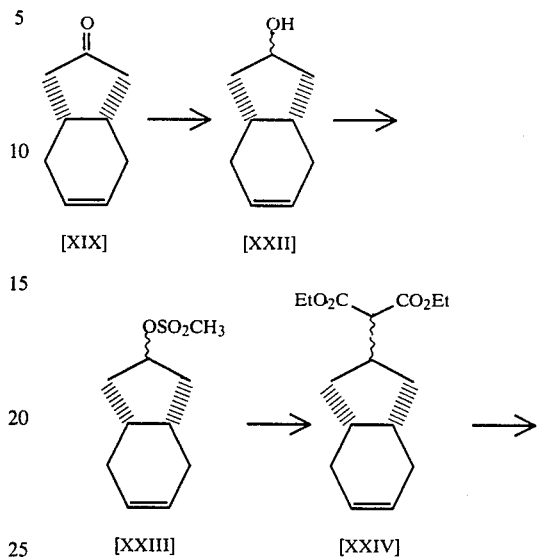

Reduction of the carbonyl compound [XIX] into the alcohol compound [XXII] can be easily carried out by a conventional procedure. The compound [XXII] can be converted into the compound [XXIII] by reacting the former with methanesulfonyl chloride and triethylamine in an inert solvent (e.g. THF) at a temperature in the range from 0° to 40° C.

The compound [XXIII] can be converted into the diester compound [XXIV] by reacting the former with diethylmalonate in the presence of sodium ethoxide in ethanol at a temperature in the range from 50° C. to boiling point of the solvent. Decarboxylation of the diester [XXIV] into the ester compound [XXV] can be carried out by heating of the former in the presence of sodium chloride in an inert solvent (e.g. DMSO) at a temperature in the range from 80° C. to a boiling point of the solvent.

Reduction of the ester [XXV] into the alcohol [XVII] can be accomplished by reacting with lithium aluminum hydride or lithium trimethoxy aluminum hydride in an inert solvent (e.g. THF) at a temperature in the range from 0° C. to a boiling point of the solvent.

The compound [XVII] can be obtained also by the process shown in the Scheme G.

Scheme G

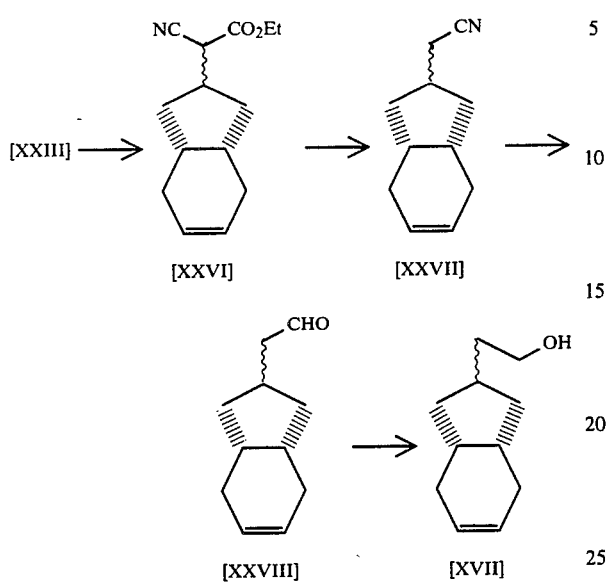

The compound [XXIII] can be converted into the compound [XXVI] by reacting of the former with ethyl cyanoacetate in the presence of sodium ethoxide in ethanol at a temperature in the range from 50° C. to a boiling point of the solvent. Decarboxylation of the ester [XXVI] into the compound [XXVII] can be carried out by heating in the presence of sodium chloride and water in an inert solvent (e.g. DMSO) at a temperature in the range from 80° C. to a boiling point of the solvent.

Reduction of the nitrile [XXVII] into the aldehyde [XXVIII] can be accomplished by reacting with diisobutyl aluminum hydride in an inert solvent (e.g. THF, ether, hexane) at a temperature in the range from −70° C. to ambient temperature. Reduction of the aldehyde [XXVIII] into the alcohol [XVII] can be easily carried out by a conventional procedure.

The alcohol compound [XVIII] used as intermidiate in the synthesis of the compound [VIII] can be prepared from the aldehyde compound [XXVIII] by the process shown in the Scheme H.

Scheme H

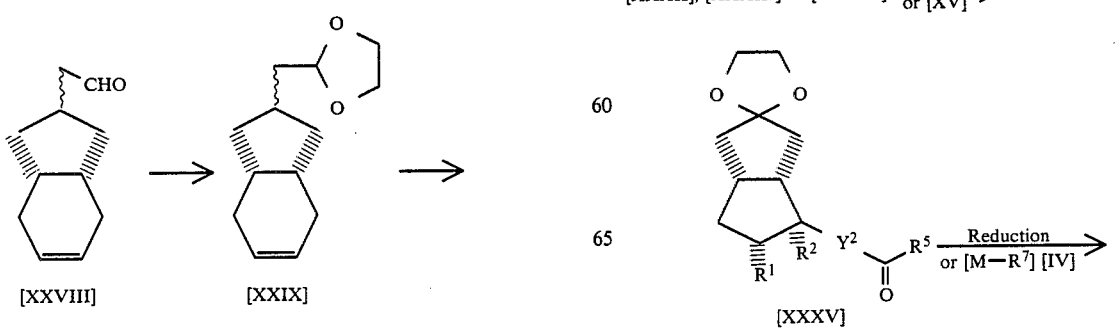

-continued
Scheme H

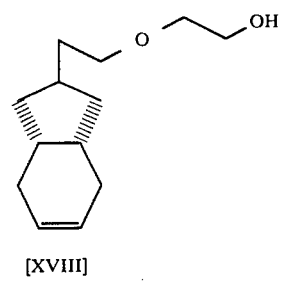

Ketalization of the aldehyde [XXVIII] into the compound [XXIX] can be easily carried out by a conventional procedure. The compound [XXIX] can be converted into the alcohol [XVIII] by reacting the former with the complex of aluminum chloride and lithium aluminum hydride in an inert solvent (e.g. ether, THF) at a temperature in the range from 20° C. to the boiling point of the solvent. The alcohol compound [V] used as an intermediate in the present invention can be prepared according to the following three paths shown in the Scheme I, J, and K. The compound [V] can be obtained from the compound [XXX] by the process shown in the Scheme I.

Scheme I

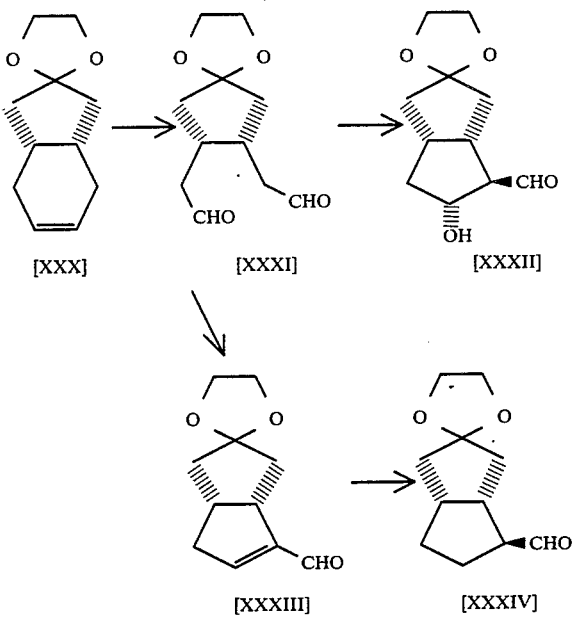

-continued
Scheme I

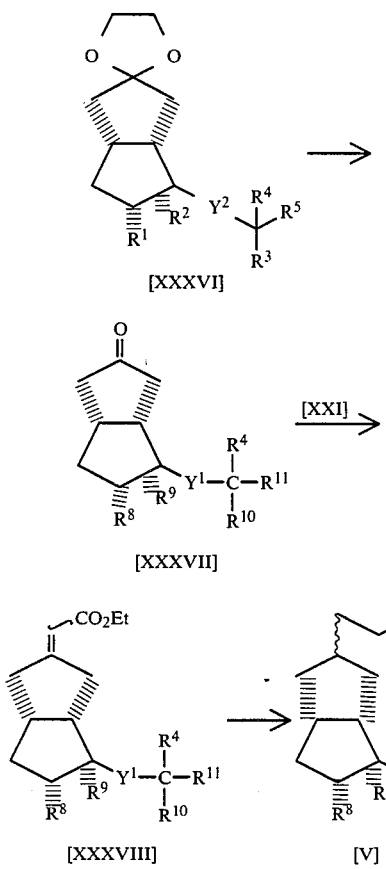

Scheme J

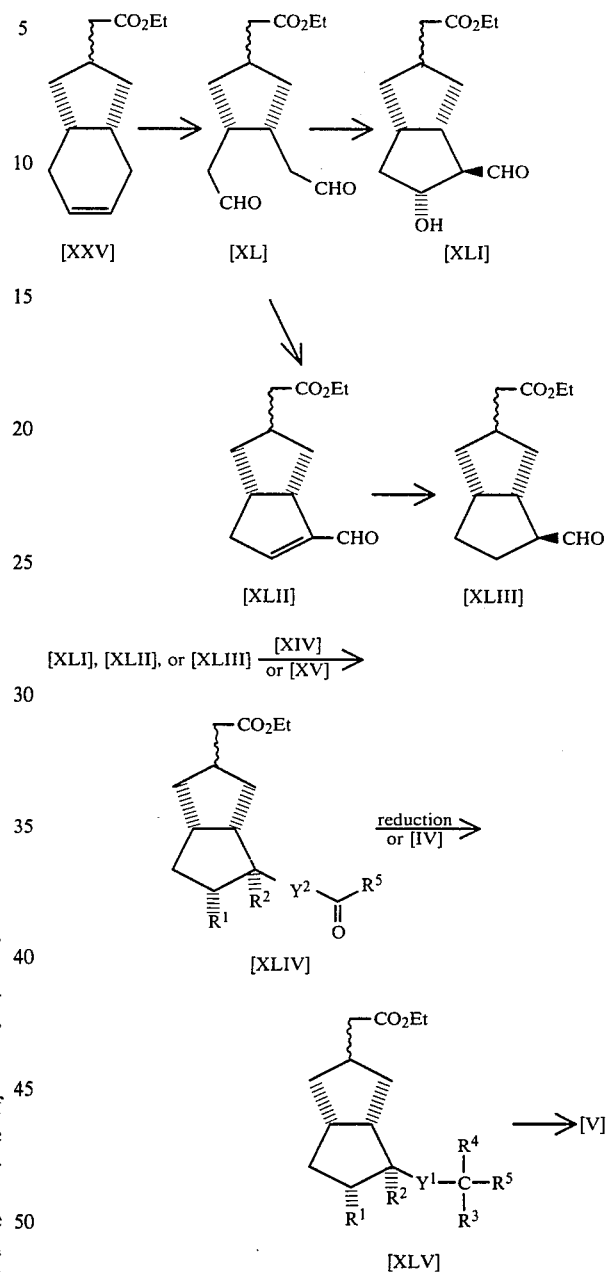

In the formula illustrated in the Scheme I, $R^1$, $R^2$, $R^3$, $R^4$, $R^5$, $R^7$, $R^8$, $R^9$, $R^{10}$, $R^{11}$, $Y^1$ and $Y^2$ are each as defined above.

The compound [XXX] be converted into the carbonyl compound [XXXV] by the same procedure as used in the synthesis of the carbonyl compound [III] shown in the Scheme C.

Reduction of the compound [XXXV] and reaction of the compound [XXXV] with the compound [IV] can be carried out by the same procedure as used in the synthesis of the compound [I] from the compound [III].

The compound [XXXVI] can be converted into the carbonyl [XXXVII] by reacting the former with pyridium p-toluenesulfonate in a solvent (e.g. acetone) at an ambient temperature, optionally followed by reduction of a vinylene group, dehydrohalogenation of halogenated vinylene group, protection of hydroxyl group. Reduction, dehydrohalogenation and protection can be carried out by the same procedure as used in the synthesis of the compound [I] shown in Schem A.

Wittig Reaction of the carbonyl compound [XXXVII] with the compound [XXI] into the compound [XXXVIII] and reduction of the compound [XXXVIII] can be carried out by the same procedure as used in the synthesis of the compound [XVII] shown in the Scheme E.

The compound [V] can be obtained from the compound [XXV] also by the process shown in the Scheme J.

The compound [XXV] can be converted into the carbonyl compound [XLIV] by the same procedure as used in the synthesis of the carbonyl compound [III] shown in the Scheme C.

The compound [XLIV] can be converted into the compound [XLV] by reacting of the former with the compound [IV] or reducing the carbonyl group, optionally followed by reduction of a vinylene group, dehydrohalogenation of a halogenated vinylene group.

The ester compound [XLV] can be converted into the compound [V] by protecting of hydroxy group and reducing of the ester group. Reduction can be carried out by the same procedure as used in the synthesis of the compound [XVII] from the compound [XXV].

The compound [V] can be obtained also from the compound [XXVII] by the process shown in the Scheme K.

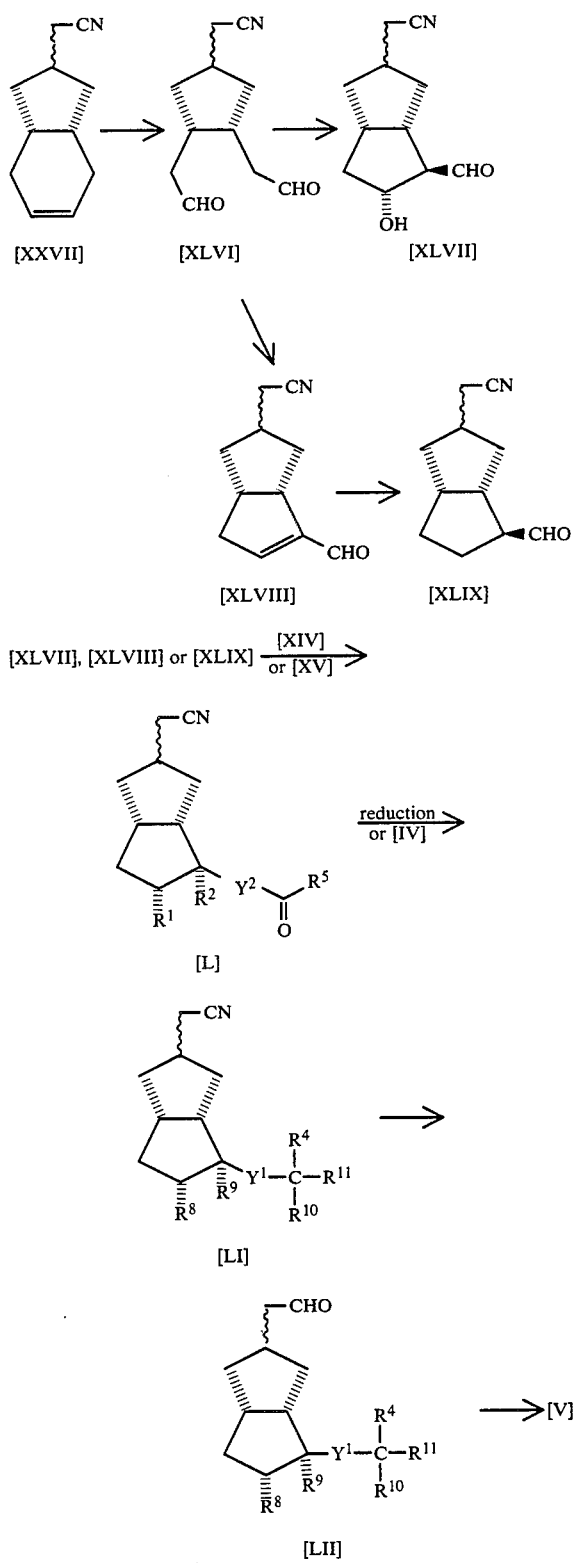

The compound [XXVII] can be converted into the carbonyl compound [L] by the same procedure as used in the synthesis of the carbonyl compound [III] shown in the The compound [L] can be converted into the compound [LI] by reacting of the former with the compound [IV] or reducing of a carbonyl group, optionally followed by reduction of a vinylene group, dehydrohalogenation of a halogenated vinylene group, and protecting hydroxyl Conversion of the compound [LI] into the compound [V] can be carried out by the same procedure as used in the synthesis of the alcohol compound from the compound [XXVII] shown in the shown in the Scheme G.

According to the present invention, the four stereoisomers of the formulae:

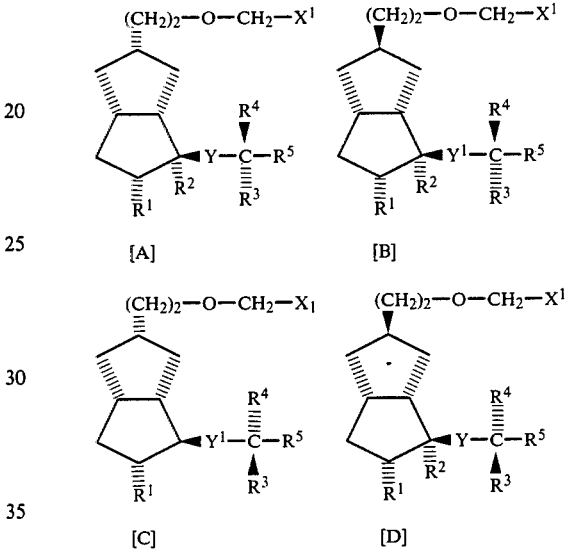

can be prepared.

In general, the bicyclooctane compound [I] can be obtained as a mixture of these stereoisomers which can be easily separated by the conventional method (e.g. column chromatography) with high purity.

If necessary, it is possible to yield selectively the bicyclooctane compound [I] of either one of these stereoisomers by changing the kinds and properties of solvents, reaction temperature, the organometalic compounds [IV] and reducing agents.

Furthermore, bicyclooctane compound [I] can be separated into optical isomers by a conventional method.

Among the bicyclooctane compounds [I] thus obtained, the compound [Ia] can be converted to its pharmacologically acceptable salt form. The pharmaceutically acceptable salts of these bicyclooctane compounds are those with pharmaceutically acceptable metal cation such as, sodium, potassium, magnesium and calcium, ammonium or amine cations.

If necessary, in order to improve the solubility in water, the bicyclooctane compounds [I] can be converted into inclusion compounds with some kinds of cyclodextrins.

The preparation of pharmaceutical compositions can be carried out by a conventional method, for example, the bicyclooctane compounds [I], they may be mixed with carriers, diluents, lubricants, fillers and/or binders such as lactose, sucrose, calcium, phosphate, starch, talcum, casein, magnesium stearate, methyl cellulose, polyglycols, tragacanth and the like, sometimes together with stabilizers and emulsifying agents. The resulting mixture may be processed in a usual manner to tablets, capsules, pills, ampoules and the like.

In a clinical practice, the bicyclooctane compounds [I] can be administered orally, subcutaneously, intravenously, intramuscularly or the like. In general, the oral administration is preffered.

The daily dosage may vary depending upon the administration route and the usual oral dosage of the active ingredient is between about 0.1 mg and about 100 mg daily for human beings.

Specific examples of the bicyclooctane compound [I] are as follows. Every compounds below has four isomers, that is, (3'α, 7α), (3'α, 7β), (3'β, 7α) and (3β, 7β).

b  2β-(3'-hydroxy-trans-1'-octenyl)-3α-hydroxy-7-(2'-carboxymethoxyethyl)-cis-bicyclo(3,3,0)octane

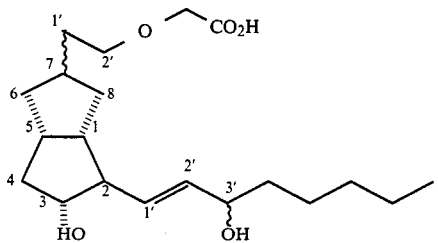

2β-(3'-hydroxy-trans-1'-nonenyl)-3α-hydroxy-7-(2'-carboxymethoxyethyl)-cis-bicyclo(3,3,0)octane 2β-(3'-hydroxy-5'-methyl-trans-1'-nonenyl)-3α-hydroxy-7-(2'-carboxymethoxyethyl)-cis-bicyclo(3,3,0)-octane 2β-(3'-hydroxy-4',4'-dimethyl-trans-1'-octenyl)-3α-hydroxy-7-(2'-carboxymethoxyethyl)-cis-bicyclo(3,3,0)octane 2β-(3'-hydroxy-4'-methyl-trans-1'-pentenyl)-3α-hydroxy-7-(2'-carboxymethoxyethyl)-cis-bicyclo(3,3,0)-octane 2β-(3'-hydroxy-4'-methyl-trans-1'-octenyl)-3α-hydroxy-7-(2'-carboxymethoxyethyl)-cis-bicyclo(3,3,0)-octane 2β-(3'-hydroxy-5',9'-dimethyl-trans-1',8'-decadienyl)-3α-hydroxy-7-(2'-carboxymethoxyethyl)-cis-bicyclo(3,3,0)octane 2β-(3'-hydroxy-4'-methylene-trans-1'-octenyl)-3α-hydroxy-7-(2'-carboxymethoxyethyl)-cis-bicyclo(3,3,0)-octane 2β-(3'-hydroxy-4',4',9'-trimethyl-trans-1',8'-decadienyl)-3α-hydroxy-7-(2'-carboxymethoxyethyl)-cis-bicyclo(3,3,0)octane 2β-(3'-hydroxy-trans-1'-cis-5'-octadienyl)-3α-hydroxy-7-(2'-carboxymethoxyethyl)-cis-bicyclo(3,3,0)-octane 2β-(3'-hydroxy-4'-methyl-trans-1'-octene-6'-ynyl)-3α-hydroxy-7-(2'-carboxymethoxyethyl)-cis-bicyclo(3,3,0)octane 2β-(3'-hydroxy-trans-1'-decene-9'-ynyl)-3β-hydroxy-7-(2'-carboxymethoxyethyl)-cis-bicyclo(3,3,0)-octane 2β-(3'-hydroxy-5'-methyl-trans-1'-decene-8'-ynyl)-3α-hydroxy-7-(2'-carboxymethoxyethyl)-cis-bicyclo(3,3,0)octane 2β-(3'-hydroxy-trans-1'-octene-5'-ynyl)-3α-hydroxy-7-(2'-carboxymethoxyethyl)-cis-bicyclo(3,3,0)-octane 2β-(3'-hydroxy-3'-(2''-isopropylidenemethyl-3'',3''-dimethylcyclopropyl)-trans-1'-propenyl)-3α-hydroxy-7-(2'-carboxymethoxyethyl)-cis-bicyclo(3,3,0)octane 2β-(3'-hydroxy-3'-cyclopentyl-trans-1'-propenyl)-3α-hydroxy-7-(2'-carboxymethoxyethyl)-cis-bicyclo(3,3,0)octane 2β-(3'-hydroxy-3'-cyclohexyl-trans-1'-propenyl-3α-hydroxy-7-(2'-carboxymethoxyethyl)-cis-bicyclo(3,3,0)octane 2β-(3'-hydroxy-3'-(1''-adamantyl)-trans-1'-propenyl)-3α-hydroxy-7-(2'-carboxymethoxyethyl)-cis-bicyclo(3,3,0)octane 2β-(3'-hydroxy-3'-norbornane-2''-yl)-trans-1'-propenyl)-3α-hydroxy-7-(2'-carboxymethoxyethyl)-cis-bicyclo(3,3,0)octane 2β-(3'-hydroxy-3'-(hexahydroindan-2''-yl)-1'trans-1'-propenyl)-3α-hydroxy-7-(2'-carboxymethoxyethyl)-cis-bicyclo(3,3,0)octane 2β-(3'-hydroxy-3'-(3''-ethylcyclopentyl)-trans-1'-propenyl)-3α-hydroxy-7-(2'-carboxymethoxyethyl)-cis-bicyclo(3,3,0)octane 2β-(3'-hydroxy-3'-(4''-methylcyclohexyl)-trans-1'-propenyl)-3α-hydroxy-7-(2'-carboxymethoxyethyl)-cis-bicyclo(3,3,0)octane 2β-(3'-hydroxy-3'-(cyclohexen-4''-yl)-trans-1'-propenyl)-3α-hydroxy-7-(2'-carboxymethoxyethyl)-cis-bicyclo(3,3,0)octane 2β-(3'-hydroxy-3'-(cyclopenten-4''-yl)-trans-1'-propenyl)-3α-hydroxy-7-(2'-carboxymethoxyethyl)-cis-bicyclo(3,3,0)octane 2β-(3'-hydroxy-3'-(bicyclo(4,3,0)nona-3''-en-8''-yl)-trans-1'-propenyl)-3α-hydroxy-7-(2'-carboxymethoxyethyl)-cis-bicyclo(3,3,0)octane 2β-(3'-hydroxy-3'-(norbornen-5''-yl)-trans-1'-propenyl-3α-hydroxy-7-(2'-carboxymethoxyethyl)-cis-bicyclo(3,3,0)octane 2β-(3',8'-dihydroxy-trans-1'-octenyl)-3α-hydroxy-7-(2'-carboxymethoxyethyl)-cis-bicyclo(3,3,0)octane 2β-(3',8'-dihydroxy-trans-1'-nonenyl)-3α-hydroxy-7-(2'-carboxymethoxyethyl)-cis-bicyclo(3,3,0)octane 2β-(3',9'-dihydroxy-trans-1'-nonenyl)-3α-hydroxy-7-(2'-carboxymethoxyethyl)-cis-bicyclo(3,3,0)octane 2β-(3',8'-dihydroxy-5'-methyl-trans-1'-octenyl-3α-hydroxy-7-(2'-carboxymethoxyethyl)-cis-bicyclo(3,3,0)octane 2β-(3'-hydroxy-3'-(2'',3''-dihydrobenzofuran-2''-yl)-trans-1'-propenyl)-3α-hydroxy-7-(2'-carboxymethoxyethyl)-cis-bicyclo(3,3,0)octane 2β-(3'-hydroxy-3'-(1'',4''-dihydrobenzodioxan-2''-yl)-trans-1'-propenyl)-3α-hydroxy-7-(2'-carboxymethoxy-ethyl)-cis-bicyclo(3,3,0)octane 2β-(3'-hydroxy-3'-(thiophen-2''-yl)-trans-1'-propenyl)-3α-hydroxy-7-(2'-carboxymethoxyethyl)-cis-bicyclo(3,3,0)octane 2β-(3'-hydroxy-3'-(pyridin-3''-yl)-trans-1'-propenyl)-3α-hydroxy-7-(2'-carboxymethoxyethyl)-cis-bicyclo(3,3,0)octane 2β-(3'-hydroxy-3'-phenyl-trans-1'-propenyl)-3α-hydroxy-7-(2'-carboxymethoxyethyl)-cis-bicyclo(3,3,0)octane 2β-(3'-hydroxy-3'-(3''-chlorophenyl)-trans-1'-propenyl)-3α-hydroxy-7-(2'-carboxymethoxyethyl)-cis-bicyclo(3,3,0)octane 2β-(3'-hydroxy-3'-(4''-fluorophenyl)-trans-1'-propenyl)-3α-hydroxy-7-(2'-carboxymethoxyethyl)-cis-bicyclo(3,3,0)octane 2β-(3'-hydroxy-3'-(3''-hydroxyphenyl)-trans-1'-propenyl)-3α-hydroxy-7-(2'-carboxymethoxyethyl)-cis-bicyclo(3,3,0)octane 2β-(3'-hydroxy-3'-(toluen-3''-yl)-trans-1'-propenyl)-3α-hydroxy-7-(2'-carboxymethoxyethyl)-cis-bicyclo(3,3,0)octane 2β-(3'-hydroxy-3'-(3''-trifluoromethylphenyl)-trans-1'-propenyl)-3α-hydroxy-7-(2'-carboxymethoxyethyl)-cis-bicyclo(3,3,0)octane 2β-(3'-hydroxy-3'-(3''-methoxyphenyl)-trans-1'-propenyl)-3α-hydroxy-7-(2'-carboxymethoxyethyl)-cis-bicyclo(3,3,0)octane 2β-(3'-hydroxy-3'-(3'',4''-dimethoxyphenyl)-trans-1'-propenyl)-3α-hydroxy-7-(2'-carboxymethoxyethyl)-cis-bicyclo(3,3,0)octane 2β-(3'-hydroxy-4'-(1'''-adamantyl)-trans-1'-butenyl)-3α-hydroxy-7-(2'-carboxymethoxyethyl)-cis-bicyclo(3,3,0)octane 2β-(3'-hydroxy-4'-cyclopentyl-trans-1'-butenyl-3α-hydroxy-7-(2'-carboxymethoxyethyl)-cis-bicyclo(3,3,0)octane 2β-(3'-hydroxy-4'-cyclohexyl-trans-1'-butenyl)-3α-hydroxy-7-(2'-carboxymethoxyethyl)-cis-bicyclo(3,3,0)octane 2β-(3'-hydroxy-4'-(3'''-ethylcyclopentyl)-trans-1'-butenyl)-3α-hydroxy-7-(2'-carboxymethoxyethyl)-cis-bicyclo(3,3,0)octane 2β-(3'-hydroxy-4'-(hexahydroindan-2''-yl)-trans-1'-butenyl)-3α-hydroxy-7-(2'-carboxymethoxyethyl)-cis-bicyclo(3,3,0)octane 2β-(3'-hydroxy-4'-(cyclohexen-4''-yl)-trans-1'-buteyl)-3α-hydroxy-7-(2'-carboxymethoxyethyl)-cis-bicyclo(3,3,0)octane 2β-(3'-hydroxy-4'-(cyclopenten-4''-yl)-trans-1-butenyl)-3α-hydroxy 7-(2'-carboxymethoxyethyl)-cis-bicyclo(3,3,0)octane 2β-(3'-hydroxy-4'-(bicyclo(4,3,0)nona-3''-en-8''-yl)-trans-1'-butenyl)-3α-hydroxy-7-(2'-carboxymethyoxyethyl)-cis-bicyclo(3,3,0)octane 2β-(3'-hydroxy-4'-(norbornen-5''-yl)-trans-1'-butenyl)-3α-hydroxy-7-(2'-carboxymethoxyethyl)-cis-bicyclo(3,3,0)octane 2β-(3'-hydroxy-4'-(imidazol-1''-yl)-trans-1'-butenyl)-3α-hydroxy-7-(2'-carboxymethoxyethyl)-cis-bicyclo(3,3,0)octane 2β-(3'-hydroxy-4'-(pyridin-3''-yl)-trans-1'-butenyl)-3α-hydroxy-7-(2'-carboxymethoxyethyl)-cis-bicyclo(3,3,0)octane 2β-(3'-hydroxy-4'-(indol-3''-yl)-trans-1'-butenyl)-3α-hydroxy-7-(2'-carboxymethoxyethyl)-cis-bicyclo(3,3,0)octane 2β-(3'-hydroxy-4'-(2'''-pyrrolidon-1''-yl)-trans-1'-butenyl)-3α-hydroxy-7-(2'-carboxymethoxyethyl)-cis-bicyclo(3,3,0)octane 2β-(3'-hydroxy-4'-(thiophen-3''-yl)-trans-1'- butenyl)-3 α-hydroxy-7-(2'-carboxymethoxyethyl)-cis-bicyclo(3,3,0)octane 2β-(3'-hydroxy-4'-(1'',2'',2'', 6'',6''-pentamethyl)-piperidin-4''-yl)-trans-1'-butenyl)-3α-hydroxy-7-(2'-carboxymethoxyethyl)-cis-bicyclo(3,3,0)octane 2β-(3'-hydroxy-5'-ethoxy-trans-1'-pentenyl)-3α-hydroxy-7-(2'-carboxymethoxyethyl)-cis-bicyclo(3,3,0)octane 2β-(3'-hydroxy-8'-methoxy-trans-1'-octenyl)-3α-hydroxy-7-(2'-carboxymethoxyethyl)-cis-bicyclo(3,3,0)octane 2β-(3'-hydroxy-7'-methoxy-trans-1'-heptenyl)-3α-hydroxy-7-(2'-carboxymethoxyethyl)-cis-bicyclo(3,3,0)octane 2β-(3'-hydroxy-4'-propoxy-trans-1'-butenyl)-3α-hydroxy-7-(2'-carboxymethoxyethyl)-cis-bicyclo(3,3,0)octane 2β-(3'-hydroxy-5'-methyl-7'-isopropoxy-trans-1'-heptenyl)-3α-hydroxy-7-(2'-carboxymethoxyethyl)-cis-bicyclo(3,3,0)octane 2β-(3'-hydroxy-4',4'-dimethyl-5'-ethoxy-trans-1'-pentenyl)-3α-hydroxy-7-(2'-carboxymethoxyethyl)-cis-bicyclo(3,3,0)octane 2β-(3'-hydroxy-5'-cyclopentyloxy-trans-1'-pentenyl)-3α-hydroxy-7-(2'-carboxymethoxyethyl)-cis-bicyclo(3,3,0)octane 2β-(3'-hydroxy-4'-cyclohexyloxy-trans-1'-butenyl)-3α-hydroxy-7-(2'-carboxymethoxyethyl)-cis-bicyclo(3,3,0)octane 2β-(3'-hydroxy-4'-(l-menthoxy)-trans-1'-butenyl)-3α-hydroxy-7-(2'-carboxymethoxyethyl)-cis-bicyclo(3,3,0)octane 2β-(3'-hydroxy-4'-(hexahydroindan-2''-yloxy)-trans-1'-butenyl)-3α-hydroxy-7-(2'-carboxymethoxyethyl)-cis-bicyclo(3,3,0)octane 2β-(3'-hydroxy-4'-(cyclohexen-4''-yloxy)-trans-1'-butenyl)-3α-hydroxy-7-(2'-carboxymethoxyethyl)-cis-bicyclo(3,3,0)octane 2β-(3'-hydroxy-4'-(cyclopenten-4''-yloxy)-trans-1'-butenyl)-3α-hydroxy-7-(2'-carboxymethoxyethyl)-cis-bicyclo(3,3,0)octane 2β-(3'-hydroxy-4'-(bicyclo(4,3,0)nona-3''-en-8''-yloxy)-trans-1'-butenyl)-3α-hydroxy-7-(2'-carboxymethoxyethyl)-cis-bicyclo(3,3,0)octane 2β-(3'-hydroxy-4'-phenyl-trans-1'-butenyl)-3α-hydroxy-7-(2'-carboxymethoxyethyl)-cis-bicyclo(3,3,0)octane 2β-(3'-hydroxy-7'-phenyl-trans-1'-heptenyl)-3α-hydroxy-7-(2'-carboxymethoxyethyl)-cis-bicyclo(3,3,0)octane 2β-(3'-hydroxy-4'-(3''-methoxyphenyl)-trans-1'- butenyl)-3α-hydroxy-7-(2'-carboxymethoxyethyl)-cis-bicyclo(3,3,0)octane 2β-(3'-hydroxy-5'-(toluen-3''-yl)-trans-1'-pentenyl)-3α-hydroxy-7-(2'-carboxymethoxyethyl)-cisbicyclo(3,3,0)octane 2β-(3'-hydroxy-4'-(2''-ethylphenyl)-trans-1'-butenyl)-3α-hydroxy-7-(2'-carboxymethoxyethyl)-cisbicyclo(3,3,0)octane 2β-(3'-hydroxy-7'-(4''-hydroxyphenyl)-trans-1'-heptenyl)-3α-hydroxy-7-(2'-carboxymethoxyethyl)-cis-bicyclo(3,3,0)octane 2β-(3'-hydroxy-4'-phenoxy-trans-1'-butenyl)-3α-hydroxy-7-(2'-carboxymethoxyethyl)-cis-bicyclo(3,3,0)octane 2β-(3'-hdyroxy-6'-phenoxy-trans-1'-hexenyl)-3α-hydroxy-7-(2'-carboxymethoxyethyl)-cis-bicyclo(3,3,0)octane 2β-(3'-hydroxy-5'-phenoxy-trans-1'-pentenyl)-3α-hydroxy-7-(2'-carboxymethoxyethyl)-cis-bicyclo(3,3,0)octane 2β-(3'-hydroxy-4'-(4''-fluorophenoxy)-trans-1'-butenyl)-3α-hydroxy-7-(2'-carboxymethoxyethyl)-cisbicyclo(3,3,0)octane 2β-(3'-hydroxy-4'-(3''-trifluolomethylphenoxy)-trans-1'-butenyl)-3α-hydroxy-7-(2'-carboxymethoxyethyl)-cis-bicyclo(3,3,0)octane 2β-(3'-hydroxy-4'-(3''-chlorophenoxy)-trans-1'-butenyl)-3α-hydroxy-7-(2'-carboxymethoxyethyl)-cisbicyclo( 3,3,0)octane 2β-(3'-hydroxy-4'-(3''-methoxyphenoxy)-trans-1'-butenyl)-3α-hydoxy-7-(2'-carboxymethoxyethyl -cis-bicyclo(3,3,0)octane 2β-(3'-hydroxy-4'-(toluen-3''-yloxy)-trans-1'-butenyl)-3α-hydroxy-7-(2'-carboxymethoxyethyl)-cis-bicyclo(3,3,0)octane 2β-(3'-hydroxy-4'-(3''-hydroxyphenoxy)-trans-1'-butenyl)-3α-hydroxy-7-(2'-carboxymethoxyethyl)-cisbicyclo(3,3,0)octane 2β-(3'-hydroxy-4'-(3'',4''-dimethoxyphenoxy)-trans-1'-butenyl)-3α-hydroxy-7-(2'-carboxymethoxyethyl)cis-bicyclo(3,3,0)octane 2β-(3'-hydroxy-3'-methyl-trans-1'-octenyl)-3α-hydroxy-7-(2'-carboxymethoxyethyl)-cis-bicyclo(3,3,0)octane 2β-(3'-hydroxy-2'-methyl-trans-1'-octenyl)-3α-hydroxy-7-(2'-carboxymethoxyethyl)-cis-bicyclo(3,3,0)octane 2β-(3'-hydroxy-trans-1'-octenyl)-7-(2'-carboxymethoxyethyl)-cis-bicyclo(3,3,0)octane 2β-(3'-hydroxy-trans-1'-octenyl)-7-(2'-carboxymethoxyethyl)-cis-bicyclo(3,3,0)oct-2-ene 2β-(3'-hydroxyoctyl)-3α-hydroxy-7-(2'-carboxymethoxyethyl)-cis-bicyclo(3,3,0)octane 2β-(3'-hydroxy-1'-octynyl)-3α-hydroxy-7-(2'-carboxymethoxyethyl)-cis-bicyclo(3,3,0)-octane 2β-(3'-acetoxy-trans-1'-octenyl)-3α-acetoxy-7-( 2'-carboxymethoxyethyl)-cis-bicyclo(3,3,0)octane 2β-(3'-benzoyloxy-trans-1'-octenyl)-3α-benzoyloxy-7-(2'-carboxymethoxyethyl)-cis-bicyclo(3,3,0)octane 2β-(3'-tetrahydropyran-2''-yloxy)-trans-1'-octenyl)-3α-(tetrahydropyran-2''-yloxy)-7-(2'-carboxymethoxyethyl)cis-bicyclo(3,3,0)octane 2β-(3'-ethoxyethyl-1''-yloxy)-trans-1'-octenyl-3α-(ethoxyethyl-1'-yloxy)-7-(2'-carboxymethoxyethyl)-cis-bicyclo(3,3,0)octane 2β-(3'-hydroxy-trans-1'-octenyl)-3α-hydroxy-7-(2'-methoxycarbonylmethoxyethyl)-cis-bicyclo-(3,3,0)octane 2β-(3'-hydroxy-trans-1'-octenyl)-3α-hydroxy-7-(2'-ethoxycarbonylmethoxyethyl)-cis-bicyclo(3,3,0)octane 2β-(3'-hydroxy-trans-1'-octenyl)-3α-hydroxy-7-(2'-phenoxycarbonylmethoxyethyl)-cis-bicyclo(3,3,0) octane P.O. 2β-(3'-hydroxy-trans-1'octenyl)3αhydroxy-7-(2'-benzyloxycarbonylmethoxyethyl)-cis-bicyclo(3,3,0)octane 2β-(3'-hydroxy-trans-1'-octenyl)-3α-hydroxy-7-(2'-methoxymethoxycarbonylmethoxyethyl)-cis-bicyclo(3,3,0)octane 2β-(3'-hydroxy-trans-1'-octenyl)-3α-hydroxy-7-(2'-acetyloxymethoxycarbonylmethoxyethyl)-cis-bicyclo(3,3,0)octane 2β-(3'-hydroxy-trans-1'-octenyl)-3α-hydroxy-7-(2'-cyclopentyloxycarbonylmethoxyethyl)-cis-bicyclo(3,3,0)octane 2β-(3'-hydroxy-trans-1'-octenyl)-3α-hydroxy-7-(2'-benzoylmethoxycarbonylmethoxyethyl)-cis-bicyclo(3,3,0)octane 2β-(3'-hydroxy-trans-1'-octenyl)-3α-hydroxy-7-(2'-(2''-hydroxyethoxycarbonylmethoxy)ethyl)-cis-bicyclo(3,3,0)octane 2β-(3'-hydroxy-trans-1'-octenyl)-3α-hydroxy-7-(2'-carbamoylmethoxyethyl)-cis-bicyclo(3,3,0)octane 2β-(3'-hydroxy-trans-1'-octenyl)-3α-hydroxy-7-(2'-dimethylcarbamoylmethoxyethyl)-cis-bicyc10(3,3,-0)octane 2β-(3'-hydroxy-trans-1'-octenyl)-3α-hydroxy-7-(2'-diethylcarbamoylmethoxyethyl)-cis-bicyclo(3,3,0)octane 2β-(3'-hydroxy-trans-1'-octenyl)-3α-hydroxy-7-(2'-cyclohexylcarbamoylmethoxyethyl)-cis-bicyclo(3,3,-0)octane 2β-(3'-hydroxy-trans-1'-octenyl)-3α-hydroxy-7-(2'-benzylcarbamoylmethoxyethyl)-cis-bicyclo(3,3,0)octane 2β-(3'-hydroxy-trans-1'-octenyl)-3α-hydroxy-7-(2'-dibenzylcarbamoylmethoxyethyl)-cis-bicyclo(3,3,-0)octane 2β-(3'-hydroxy-trans-1'-octenyl)-3α-hydroxy-7-(2'-(N-benzylphenylcarbamoylmethoxy)ethyl)-cis-bicyclo(3,3,0)octane 2β-(3'-hydroxy-trans-1'-octenyl)-3α-hydroxy-7-(2'-pyrrolidinocarbonylmethoxyethyl)-cisbicyclo(3,3,0)octane 2β-(3'-hydroxy-trans-1'-octenyl)-3α-hydroxy-7-(2'-phenylcarbamoylmethoxyethyl)-cis-bicyclo(3,3,0)octane 2β-(3'-hydroxy-trans-1'-octenyl)-3α-hydroxy-7-(2'-morpholinocarbonylmethoxyethyl)-cis-bicyclo(3,3,-0)octane Practical and preferred embodiments of the present invention are illustratively shown in the following example, which are not intended to limit the scope of the invention thereto.

REFERENTIAL EXAMPLE 1

A tetrahydrofuran solution (100 ml) of 8-oxo-cis-bicyclo[4,3,0]nona-3-ene (80g) was added to a tetrahydrofuran solution (1000 ml) of the ylide prepared with triethyl phosphonoacetate (160 g) and sodium hydride (60% mineral oil dispersion, 23.5 g). The mixture was stirred for 30 min. at room temperature and poured into water and then extracted with ethylacetate. The organic layer was washed with water, dried, concentrated under reduced pressure to give 8-ethoxycarbonylmethylene-cis-bicyclo[4,3,0]nona-3-ene.

NMR δ (CDCl$_3$) 4.14 (2H, q, J=7Hz), 5.61 (2H, br), 5.80 (1H, m).

IR $\nu_{cm-1}^{film}$: 2900, 1705.

REFERENTIAL EXAMPLE 2

To liquid ammonia (850 ml), was added a mixed solution of 8 ethoxycarbonylmethylene-cis-bicyclo[4,3,0]-nona-3-ene (24.8 g), ethanol (180 ml) and ether (70 ml) at −50° C., and then the mixture was stirred for 10 minutes. Lithium (9.6 g) was added by portions, and then the mixture was stirred for 2 hr at −50° C. Ammonia was evaporated and the mixture was poured into water, extracted with ethylacetate. The extract was washed with water, dried, concentrated and then chromatographed to give 8-(2'-hydroxyethyl)-cis-bicyclo[4,3,0]nona-3-ene.

NMR δ(CDCl$_3$) 3.68 (2H, t, J=7Hz), 5.67 (2H, brds).

REFERENTIAL EXAMPLE 3

To an ethanol suspension (250 ml) of sodium borohydride (7.2 g), was added 8-oxo-cis-bicyclo[4,3,0]-nona-3-ene (100 g). The mixture was stirred for 2 hr at 5° C. to 10° C. and poured into water, and then extracted with ethylacetate. The organic layer was washed with water, dried, concentrated under reduced pressure to give 8-hydroxy-cis-bicyclo[4,3,0]nona-3-ene.

NMR δ(CCl$_4$) 4.0-4.5 (1H, m), 5.65 (2H, m).

REFERENTIAL EXAMPLE 4

To a mixed solution of 8-hydroxy-cis-bicyclo-[4,3,0]nona-3-ene (109 g), triethylamine (160 g) and toluene (200 ml), was added methanesulfonyl chloride (110 g) at 0° C. to 5° C. After stirred for one hour, the reaction mixture was poured into water and then extracted with ethylacetate. The organic layer was washed with water, dried, and concentrated to give 8-methanesulfonyl-oxy-cis-bicyclo[4,3,0]nona-3-ene.

IR $_{cm-1}^{film}$: 2930, 1655, 1430, 1350, 1180, 935, 885.

Sodium (18 g) was added to ethanol (300 ml) by portions at room temperature. After the sodium chips disappeared, a ethanol solution (200 ml) of diethyl malonate (131 g) was added and stirred for 30 min. An ethanol solution (200 ml) of 8-methanesulfonyloxy-cis-bicyclo[4,3,0]nona-3-ene (160 g) obtained above was added at room temperature and then the mixture was stirred under reflux for 7 hr. The mixture was cooled and poured into water, and extracted with toluene. The organic layer was dried, concentrated, and then distilled in vacuo to give 8-(diethoxycarbonyl)methyl-cis-bicyclo-[4,3,0]nona-3-ene.

bp. 125°–140° C./0.2 mm Hg.

REFERENTIAL EXAMPLE 5

To a mixed solution of 8-(diethoxycarbonyl)-methyl-cis-bicyclo[4,3,0]nona-3-ene (129 g), dimethyl-sulfoxide (600 ml), water (12 g), was added sodium chloride (19 g), and then the mixture was heated under reflux for 7 hr. The mixture was poured into water, and extracted with n-hexane. The organic layer was dried, concentrated, and then distilled in vacuo to give 8-ethoxycarbonyl-methyl-cis-bicyclo[4, 3,0]nona-3-ene.

bp. 107°–125° C./0.2 mm Hg.

REFERENTIAL EXAMPLE 6

To a tetrahydrofuran suspension (250 ml) of lithium aluminum hydride (1.14 g), was added a tetrahydrofuran solution of 8-ethoxycarbonylmethyl-cis-bicyclo[4,3,0]nona-3-ene (10.4 g), and the mixture was stirred under reflux for 3 hr. The mixture was cooled to 0°–5° C., and treated by successive dropwise addition of water (1 ml), 15% sodium hydroxide solution (1 ml), water (3 ml). A dry granular precipitate was filtered out and the mother liquor was concentrated to give 8-(2'-hydroxyethyl)-cis-bicyclo[4,3,0]nona-3-ene.

REFERENTIAL EXAMPLE 7

Sodium hydride (4.0 g, 60% mineral oil dispersion) was added to a toluene solution (300 ml) of 8-(2'-hydroxyethyl)-cis-bicyclo[4,3,0]nona-3-ene (15 g). After the mixture was stirred under reflux for one hour, a toluene solution (100 ml) of N-benzyl-N-phenylchloroacetamide (22 g) was added at 70°–80° C. After stirred under reflux for one hour, the mixture was poured into water and extracted with ethyl acetate. The extract was washed with water, dried over MgSO$_4$ and concentrated to give an oil. This material was chromatographed on silica gel to give 8-(2'-(N-benzylphenylcarbamoylmethoxy)ethyl)-cis-bicyclo[4,3,0-]nona-3-ene as an oil.

NMR δ(CDCl$_3$) 3.42 (2H, t, J=7Hz), 3.79 (2H, s), 4.85 (2H, s), 5.60 (2H, brds).

IR $_{cm-1}^{film}$: 2920, 1660.

REFERENTIAL EXAMPLE 8

According to the same procedure as Referential Example 7, there were obtained the following compounds.

8-(2'-dibenzylcarbamoylmethoxyethyl)-cis-bicyclo[4,3,0]nona-3-ene.

NMR δ(CDCl$_3$) 3.53 (2H, t, J=7Hz), 4.33 (2H, s), 4.56 (4H, brds), 5.63 (2H, m).

IR $_{cm-1}^{film}$: 2920 1650.

8-(2'-diethylcarbamoylmethoxyethyl)-cis-bicyclo[4,3,0-]nona-3-ene.

NMR δ(CDCl$_3$) 3.33 (4H, q, J=7Hz), 3.49 (2H, t, J=6Hz) 4.11 (2H, s), 5.63 (2H, brds).

IR$_{cm-1}^{film}$: 2940 1650.

8-(2'-methoxycarbonylmethoxyethyl)-cis-bicyclo[4,3,0-]nona-3-ene.

NMR δ(CDCl$_3$) 3.51 (2H, t, J=6Hz), 3.78 (3H, s), 4.07 (2H, s), 5.65 (2H, brds).

IR$_{cm-1}^{film}$: 2940, 1755, 1740 cm$^{-1}$.

REFERENTIAL EXAMPLE 9

A methanol solution (500 ml) of 8-(2'-(N-benzylphenylcarbamoylmethoxy)ethyl)-cis-bicyclo[4,3,0]-nona-3-ene (22 g) was subjected to a stream of ozonized oxygen at −50° to −60° C. After the starting material was disappeared, dimethylsulfide (50 ml) was added and the mixture was stirred for 2 hr at −20° to 0° C. The mixture was then concentrated by introduction of a stream of nitrogen to give an oily dialdehyde. The dialdehyde thus obtained was dissolved in methanol (300 ml) and an aqueous sodium hydroxide (5%, 200 ml) was added at 5° to 10° C. The mixture was stirred for 1 hr at the same temperature and then poured into a mixture of water and ethylacetate. After separation, the organic layer was washed with water, dried and concentrated under reduced pressure to give an oily 2β-formyl-3α-hydroxy-7-(2'-(N-benzylphenylcarbamoylmethoxy)-ethyl)-cis-bicyclo[3,3,0]octane.

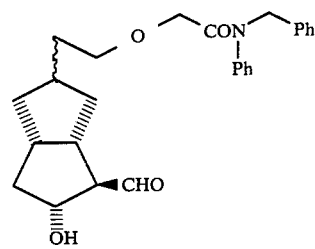

A tetrahydrofuran solution (THF, 100 ml) of the aldol obtained above was added to THF solution (500 ml) of the ylide prepared with dimethyl(2-oxo-heptyl)-phosphonate (20 g) and sodium hydride (60%, 2.32 g). The mixture was stirred for 1 hr at room temperature, and then poured into water, and extracted with ethylacetate. The extract was washed with water, dried and concentrated under reduced pressure and then chromatographed on silica gel to give 2β(3'-oxo-trans-1'-octenyl)-3α-hydroxy-7-(2'-(N-benzylphenylcarbamoylmethoxy)ethyl)-cis-bicyclo[3,3,0]octane.

NMR δ(CDCl$_3$) 3.67 (1H, m), 3.80 (2H, s) 4.87 (2H, s), 6.18 (1H, d, J=16Hz).

IR$_{cm-a}^{film}$: 3420, 2930, 1660.

REFERENTIAL EXAMPLE 10

A THF solution (30 ml) of 2β-formyl-3α-hydroxy-7-(2'-diethylcarbamoylmethoxyethyl)-cis-bicyclo-

[3,3,0]octane (3.5 g) which was obtained according to the same procedure as Referential Example 9 was added to a THF solution (150 ml) of the ylide prepared with dimethyl(2-oxo-hepthyl)phosphonate (5 g) and sodium hydride (60%, 0.5 g). The mixture was stirred for one hour at room temperature, and then poured into water, and extracted with ethylacetate. The extract was washed with water, dried, concentrated and then chromatographed to give an oil containing 2β-(3'-oxo-trans-1'-octenyl)-3α-hydroxy-7-(2'-diethylcarbamoylmethoxyethyl)-cis-bicyclo[3,3,0]octane.

To a dichloromethane solution (100 ml) of the oil obtained above, was added dihydropyran (1.0 g) and pyridinium p-toluenesulfonate (500 mg), and the mixture stirred at room temperature for 5 hr. The mixture was poured into sodium bicarbonate aqueous solution, and extracted with ethylacetate. The extract was dried, concentrated and chromatographed to give 2β-(3'-oxo-trans-1'-octenyl)-3α-(tetrahydropyran-2'-yloxy)-7-(2'-diethyl-carbamoylmethoxyethyl)-cis-bicyclo[3,3,0]octane.

NMR δ(CDCl$_3$) 4.10 (2H, s), 4.55 (1H, m) 6.13 (1H, d, J=16Hz).

IR$_{cm-a}^{film}$: 2930 1660.

REFERENTIAL EXAMPLE 11

According to the same procedures as Referential Example 9 or 10, there were obtained the following compounds.

2β-(3'-oxo-trans-1'-nonenyl)-3α-hydroxy-7-(2'-(N-benzylphenylcarbamoylmethoxy)ethyl)-cis-bicyclo[3,3,0]-octane.

NMR δ(CDCl$_3$) 3.83 (2H, s), 4.88 (2H, s), 6.14 (1H, d, J=16Hz).

IR$_{cm31}$ $^{film}$: 3430, 2930, 1660.

2β-(3'-oxo-4'methyl-trans-1'-pentenyl)-3α-hydroxy-7-(2'-(N-benzylphenylcarbamcylmethoxy)ethyl)-cis-bicyclo[3,3,0]octane.

NMR δ(CDCl$_3$) 1.11 (6H, d, J=7Hz), 3.83 (2H, s) 4.88 (2H, s), 6.22 (1H, d, J=16Hz).

IR$_{cm-}$$^{film}$: 3430, 2920, 1660.

2β-(3'-oxo-5'-methyl-trans-1'-hexenyl)-3α-hydroxy-7-(2'-(N-benzylphenylcarbamoylmethoxy)ethyl)-cis-bicyclo[3,3,0]octane.

NMR δ(CDCl$_3$) 0.92 (6H, d, J=7Hz), 3.82 (2H, s) 4.87 (2H, s), 6.14 (1H, d, J=16Hz).

IR$_{cm-}$$^{film}$: 3420, 2920, 1665.

2β-(3'-oxo-5'-methyl-trans-1'-nonenyl)-3α-hydroxy-7-(2'-(N-benzylphenylcarbamoylmethoxy)ethyl)-cis-bicyclo[3,3,0]octane.

NMR δ(CDCl$_3$) 0.88 (6H, m), 6.10 (1H, d, J=16Hz).

IR$_{cm-}$$^{film}$: 3430, 2930, 1660.

2β-(3'-oxo-4'-cthyl-trans-1'-octenyl)-3α-hydroxy-7-(2'-(N-benzylphenylcarbamoylmethoxy)ethyl)-cis-bicyclo[3,3,0]octane NMR δ(CDCl$_3$) 0.88 (6H, m), 3.86 (2H, s) 4.90 (2H, s), 6.28 (1H, d, J=16Hz).

IR$_{cm-}$$^{film}$: 3420, 2920, 1660.

2β-(3'-oxo-4',4'-dimethyl-trans-1'-octenyl)-3α-hydroxy-7-(2'-(N-benzylphenylcarbamoylmethoxy)ethyl)-cis-bicyclo[3,3,0]octane NMR δ(CDCl$_3$) 1.10 (6H, s), 3.81 (2H, s) 4.98 (2H, s), 6.50 (1H, d, J=16Hz).

2β-(3'-oxo-4'-methylene-trans-1'-octenyl)-3α-hydroxy-7-(2'-(N-benzylphenylcarbamoylmethoxy)ethyl)-cis-bicyclo[3,3,0]octane.

NMR δ (CDCl$_3$) 4.83 (2H, s), 5.65 (1H, br) 5.90 (1H, s), 6.57 (1H, d, J=16 Hz).

IR$_{cm-}$$ν^{film}$: 3430, 2930, 1660.

2β-(3'-oxo-5',9'-dimethyl-trans-1',8'-decadienyl)-3α-hydroxy-7-(2'-(N-benzylphenylcarbamoylmethoxy)ethyl)-cis-bicyclo[3,3,0]octane.

NMR δ (CDCl$_3$) 0.88 (3H, d, J=6 Hz), 1.53 (3H, s) 1.67 (3H, s), 4.87 (2H, s) 6.12 (1H, d, J=16 Hz).

IR$_{cm-}$$ν^{film}$: 3420, 2920, 1665.

2β-(3'-oxo-4'-methyl-trans-1'-octen-6'-ynyl)-3α-hydroxy-7-(2'-(N-benzylphenylcarbamoylmethoxy)ethyl)cis-bicyclo[3,3,0]octane.

NMR δ (CDCl$_3$) 1.73 (3H, t, J=3 Hz), 4.89 (2H, s) 6.20 (1H, d, J=16 Hz).

IR$_{cm-}$$ν^{film}$: 3420, 2930, 1660.

2β-(3'-oxo-3'-cyclopentyl-trans-1'-propenyl)-3α-hydroxy-7-(2'-(N-benzylphenylcarbamoylmethoxy)ethyl-cis-bicyclo[3,3,0]octane.

NMR δ (CDCl$_3$) 3.82 (2H, s), 4.86 (2H, s), 6.20 (1H, d, J=16 Hz).

IR$_{cm-}$$ν^{film}$: 3420, 2920, 1660.

2β-(3'-oxo-3'-cyclohexyl-trans-1'-propenyl)-3α-hydroxy-7-(2'-(N-benzylphenylcarbamoylmethoxy)ethyl)cis-bicyclo[3,3,0]octane.

NMR δ (CDCl$_3$) 3.82 (2H, s), 4.89 (2H, s), 6.22 (1H, d, J=16 Hz).

IR$_{cm-}$$ν^{film}$: 3420, 2920, 1660.

2β-(3'-oxo-3'-cyclohexyl-trans-1'-propenyl)-3α-hydroxy-7-(2'-dibenzylcarbamoylmethoxyethyl)-cis-bicyclo[3,3,0]octane.

NMR δ (CDCl$_3$) 4.51 (4H, br), 6.24 (1H, d, J=16 Hz).

IR$_{cm-}$$ν^{film}$: 3420, 2920, 1665.

2β-(3'-oxo-3'-(2''-isopropylidenemethyl-3'',3''-dimethylcyclopropyl)-trans-1'-propenyl)-3α-hydroxy-7-(2'-(N-benzylphenylcarbamoylmethoxy)ethyl)cis-bicyclo[3,3,0]octane.

NMR δ (CDCl$_3$) 4.83 (2H, s), 6.27 (1H, d, J=16 Hz).

IR$_{cm-}$$ν^{film}$: 3430, 2920, 1660.

2β-(3'-oxo-3'-(cyclohexen-4''-yl)-trans-1'-propenyl)-3α-hydroxy-7-(2'-(N-benzylphenylcarbamoylmethoxy)ethyl)-3α-hydroxy-cis-bicyclo[3,3,0]octane.

NMR δ (CDCl$_3$) 3.83 (2H, s), 4.88 (2H, s) 5.70 (2H, br), 6.28 (1H, d, J=16 Hz).

IR$_{cm-}$$ν^{film}$: 3400, 2920, 1665.

2β-(3'-oxo-3'-(bicyclo[4,3,0]nona-3''-en-8''-yl)-trans-1'-propenyl)-3α-hydroxy-7-(2'-(N-benzylphenylcarbamoylmethoxy)ethyl)-cis-bicyclo[3,3,0]octane.

NMR δ (CDCl$_3$) 3.83 (2H, s), 4.88 (2H, s) 5.62 (2H, brs), 6.20 (1H, d, J=16 Hz).

IR$_{cm-}$$ν^{film}$: 2430, 2930, 1665.

2β-(3'-oxo-3'-(4''-fluorophenyl)-trans-1'-propenyl)-3α-hydroxy-7-(2'-(N-benzylphenylcarbamoylmethoxy)ethyl)-cis-bicyclo[3,3,0]octane.

NMR δ (CDCl$_3$) 3.82 (2H, s), 4.87 (2H, s) 6.93–7.37 (12H, m), 7.90–8.08 (2H, m).

IR$_{cm-}$$ν^{film}$: 3400, 2920, 1660.

2β-(3'-oxo-4'-(1''-adamantyl)-trans-1'-butenyl)-3α-hydroxy-7-(2'-(N-benzylphenylcarbamoylmethoxy)ethyl)-cis-bicyclo[3,3,0]octane.

NMR δ (CCDCl$_3$) 3.83 (2H, s), 4.88 (2H, s) 6.13 (1H, d, J=16 Hz).

IR$_{cm-}$$ν^{film}$: 3430, 2900, 1660.

2β-(3'-oxo-4'-(bicyclo[4,3,0]nona-3''-en-8''-yl)-trans-1'-butenyl)-3α-hydroxy-7-(2'-(N-benzylphenylcarbamoylmethoxy)ethyl)-cis-bicyclo[3,3,0]octane.

NMR δ (CDCl$_3$) 3.81 (2H, s), 4.89 (2H, s) 5.68 (2H, brs), 6.14 (1H, d, J=16 Hz) 6.77 (1H, dd, J=16 Hz and 7 Hz).

IR$_{cm-}$$ν^{film}$: 3400, 2920, 1660.

2β-(3'-oxo-4'-(l-menthoxy)-trans-1'-butenyl)-3α-(tetrahydropyran-2'-yloxy)-7-(2'-(N-benzylphenylcarbamoylmethoxy)ethyl)-cis-bicyclo[3,3,0]octane.

NMR δ (CDCl₃) 0.78 (3H, d, J=7 Hz), 0.88 (6H, d, J=7 Hz), 4.88 (2H, s), 6.29 (1H, d, J=16 Hz).

IR$_{cm^{-1}}^{film}$: 2920, 1660.

2β-(3'-oxo-4'-(4''-fluorophenoxy)-trans-1'-butenyl)-3α-(tetrahydropyran-2'-yloxy)-7-(diethylcarbamoylmethoxyethyl)-cis-bicyclo[3,3,0]octane.

NMR δ (CDCl₃) 4.10 (2H, s), 4.52 (1H, m) 4.65 (2H, s), 6.46 (1H, d, J=16 Hz).

IR$_{cm^{-1}}^{film}$: 2930, 1660.

2β-(3'-oxo-4'-phenoxy-trans-1'-butenyl)-3α-hydroxy-7-(2'-(N-benzylphenylcarbamoylmethoxy)ethyl)-cis-bicyclo[3,3,0]octane.

NMR δ (CDCl₃) 3.82 (2H, s), 4.69 (2H, s) 4.88 (2H, s), 6.49 (1H, d, J=16 Hz).

IR$_{cm^{-1}}^{film}$: 3400, 2900, 1660.

REFERENTIAL EXAMPLE 12

A methanol solution (160 ml) of 8-(2'-(N-benzylphenylcarbamoylmethoxy)ethyl)-cis-bicyclo[4,3,0]nona-3-ene (4.5 g) was subjected to a streamed of ozonized oxygen at −50° to −60° C. After the starting material was disappeared, dimethylsulfide (120 ml) was added and the mixture was stirred for 2 hr at −20° to 0° C. The mixture was then concentrated by introduction of a stream of nitrogen to give an oily dialdehyde.

The dialdehyde thus obtained was dissolved in methanol (250 ml) and potassium carbonate (2.5 g) was added at room temperature. The mixture was stirred for 2.5 hr and was poured into water and then extracted with ethyl acetate.

The extract was washed with water, dried and concentrated under reduced pressure to give 2-formyl-7-(2'-(N-benzylphenylcarbamoylmethoxy)ethyl)-cis-bicyclo[3,3,0]oct-2-ene.

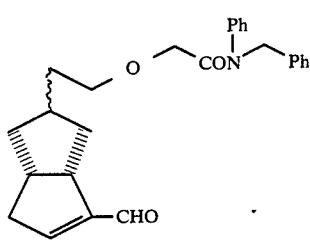

A tetrahydrofuran solution (75 ml) of the aldehyde (3.5 g) obtained above was added to a tetrahydrofuran solution (425 ml) of the ylide prepared with dimethyl-2-oxo-4-ethoxyphosphonate (9.5 g) and sodium hydride (60%, 1.14 g). The mixture was stirred for 2 hr at room temperature and poured into water and then extracted with ethylacetate. The organic layer was washed with water, dried, concentrated under reduced pressure and then chromatographed to give 2-(3'-oxo-5'-ethoxy-trans-1'-pentenyl)-7-(2'-(N-benzylphenylcarbamoylmethoxy)ethyl)-cis-bicyclo[3,3,0]oct-2-ene.

NMR δ (CDCl₃) 1.13 (3H, t, J=7 Hz), 3.80 (2H, s), 4.88 (2H, s), 6.04 (1H, d, J=16 Hz) 6.10 (1H, br).

REFERENTIAL EXAMPLE 13

A dimethoxyethane solution (DME, 100 ml) of dimethyl (2-oxo-2-cyclopenthylethyl)phosphonate (6.6 g) was added to a DME suspension (200 ml) of sodium hydride (60%, 1.0 g), and the mixture was stirred for 0.5 hr. N-Bromosuccinimide (4.45 g) was added at room temperature, and then the mixture was stirred for one hr. A DME solution (100 ml) of 2β-formyl-3α-hydroxy-7-(2'-(N-benzylphenylcarbamoylmethoxy)ethyl)-cis-bicyclo[3,3,0]octane (9 g) was added and the mixture was stored for 5 hr. The mixture was poured into the water and extracted with ethyl acetate. The extract was washed with water, dried, concentrated, and chromatographed to give 2β-(2'-bromo-3'-oxo-3'-cyclopentyl-1'-trans-propenyl)-3α-hydroxy-7-(2'-(N-benzylphenylcarbamoylmethoxy)ethyl)-cis-bicyclo-[3,3,0]octane.

NMR δ (CDCl₃) 3.48 (2H, m), 3.88 (2H, s), 4.90 (2H, s).

IR$_{cm^{-1}}^{film}$: 2920, 1665.

REFERENTIAL EXAMPLE 14

According to the same procedure as Referential Example 13, there were obtained the following compounds.

2β-(2'-bromo-3'-oxo-4'-methyl-trans-1'-pentenyl)-3α-hydroxy-7-(2'-(N-benxylphenylcarbamoylmethoxy)ethyl)-cis-bicyclo[3,3,0]octane.

NMR δ (CDCl₃) 1.13 (6H, d, J=7 Hz), 3.82 (2H, s) 4.86 (2H, s), 6.8–7.3 (11H, br).

IR$_{cm^{-1}}^{film}$: 3400, 2920, 1660.

2β-(2'-bromo-3'-oxo-5',9'-dimethyl-trans-1',8'-decadinyl)-3α-hydroxy-7-(2'-(N-benzylphenylcarbamoylmethoxy)ethyl)-cis-bicyclo[3,3,0]octane.

NMR δ (CDCl₃) 0.92 (3H, d, J=6 Hz), 3.82 (2H, s) 4.80 (2H, s), 5.09 (1H, t-like).

IR$_{cm^{-1}}^{film}$: 3400, 2910, 1660.

2β-(2'-bromo-3'-oxo-5'-methyl-trans-1'-nonenyl)-3α-hydroxy-7-(2'-N-benzylphenylcarbamoylmethoxy)ethyl)-cis-bicyclo[3,3,0]octane.

NMR δ (CDCl₃) 0.88 (6H, m), 3.82 (2H, s) 6.85–7.4 (11H, br).

IR$_{cm^{-1}}^{film}$: 3400, 2920, 1665.

2β-(2'-bromo-3'-oxo-4'-methyl-trans-1'-octen-6'-ynyl)-3α-hydroxy-7-(2'-(N-benzylphenylcarbamoylmethoxy)ethyl)-cis-bicyclo[3,3,0]octane.

NMR δ (CDCl₃) 1.74 (3H, t, J=3 Hz), 4.89 (2H, s) 6.85–7.4 (11H, br).

IR$_{cm^{-1}}^{film}$: 3400, 2920, 1660.

EXAMPLE 1

To a methanol solution (100 ml) of 2β-(3'-oxo-trans-1'-octenyl)-3α-hydroxy-7-(2'-(N-benzylphenylcarbamoylmethoxy)ethyl)-cis-bicyclo[3,3,0]octane (3.7 g) was added sodium borohydride (300 mg), and the mixture was stirred for 2 hr. at −30° C. to −20° C. After the starting material was disappeared, the mixture was poured into water and extracted with ethyl acetate. The extract was washed with water, dried, concentrated at reduced pressure and then chromatographed to give oily two isomers. Less polar isomer was termed Fr-1 and more polar one was termed Fr-2.

To a chloroform solution (10 ml) of Fr-1 (400 mg) obtained above, was added manganese oxide (200 mg), and then the mixture was stirred for 10 hr. The precipitate was filtered out, and the mother liquor was concentrated and chromatographed to give 2β-(3'-oxo-trans-1'-octenyl)-3α-hydroxy-7-(2'-(N-benzylphenylcarbamoylmethoxy)ethyl)-cis-bicyclo[3,3,0]octane. This enone compound was reduced according to the procedure mentioned above and chromatographed to give two isomers which were the same products as Fr-1 and Fr-2 obtained above. Therefore Fr-1 and Fr-2 were regarded as stereo isomers at 3'-carbon of ω-chain.

Fr-1 2β-(3'β-hydroxy-trans-1'-octenyl)-3α-hydroxy-7-(2'-(N-benzylphenylcarbamoylmethoxy)ethyl)-cis-bicyclo[3,3,0]octane.

NMR δ (CDCl₃) 3.63 (1H, m), 3.82 (2H, s) 4.06 (1H, m), 4.86 (2H, s), 5.53 (2H, m).

Fr-2 2β-(3'α-hydroxy-trans-1'-octenyl)-3α-hydroxy-7-(2'-(N-benzylphenylcarbamoylmethoxy)ethyl)-cis-bicyclo[3,3,0]octane.

NMR δ (CDCl₃) 3.60 (1H, m), 3.83 (2H, s), 3.98 (1H, m) 4.90 (2H, s), 5.46 (2H, m).

EXAMPLE 2

Lithium triisobutylborohydride (3 ml, 1M solution in THF) was added to a THF solution (25 ml) of 2β-(3'-oxo-4'-methyl-trans-1'-octen-6'-ynyl)-3α-hydroxy-7-(2'-(N-benzylphenylcarbamoylmethoxy)ethyl)-cis-bicyclo[3,3,0]octane (1.0 g) at −50° C. to −60° C. The mixture was stirred for one hour at the same temperature, and then poured into water and extracted with ethyl acetate. The extract was washed with water, dried, concentrated and then chromatographed to give 2β-(3'β-hydroxy-4'-methyl-trans-1'-octen-6'-ynyl)-3α-hydroxy-7-(2'-(N-benzylphenylcarbamoylmethoxy)ethyl)-cis-bicyclo[3,3,0] octane.

NMR δ (CDCl₃) 3.83 (2H, s), 3.98 (1H, m) 4.89 (2H, s), 5.57 (2H, m).

and 2β-(3α-hydroxy-4'-methyl-trans-1'-octen-6'-ynyl)-3α-hydroxy-7-(2'-(N-benzylphenylcarbamoylmethoxy)ethyl)-cis-bicyclo[3,3,0]octane.

NMR δ (CDCl₃) 3.83 (2H, s), 3.98 (1H, m) 4.88 (2H, s) 5.53 (2H, m).

EXAMPLE 3

In the same manner as Example 1, using 2β-(3'-oxo-trans-1'-octenyl)-3α-(tetrahydropyran-2'-yloxy)-7-(2'-diethylcarbamoylmethoxy)ethyl)-cis-bicyclo[3,3,0]octane obtained in Referential Example 10, there was obtained 2β-(3'-hydroxy-trans-1'-octenyl)-3α-(tetrahydropyran-2'-yloxy)-7-(2'-diethylcarbamoylmethoxyethyl)-cis-bicyclo[3,3,0]octane.

NMR δ (CDCl₃) 4.10 (2H, s), 4.63 (1H, m), 5.52 (2H, m).

To an ethanol solution (30 ml) of the compound obtained above, was added pyridinium p-toluenesulfonate (100 mg), and the mixture was stirred at 50° C. to 60° C. for 5 hr. After the starting material was disappeared, the mixture was poured into water and extracted with ethyl acetate. The extract was washed with water, dried, concentrated at reduced pressure and then chromatographed o to give 2β-(3'-hydroxy-trans-1'-octenyl)-3α-hydroxy-7-(2'-diethylcarbamoylmethoxyethyl)-cis-bicyclo[3,3,0]octane.

NMR δ (CDCl₃) 4.03 (1H, m) 4.10 (2H, s) 5.50 (2H, m).

EXAMPLE 4

According to the same procedure as Example 1, Example 2, or Example 3, there were obtained the following compounds.

2β-(3β-hydroxy-trans-1'-nonenyl)-3α-hydroxy-7-(2'-(N-benxylphenylcarbamoylmethoxy)ethyl)-cis-bicyclo[3,3,0]octane.

NMR δ (CDCl₃) 3.66 (1H, m), 3.83 (2H, s) 4.08 (1H, m), 5.60 (2H, m).

2β-(3'α-hydroxy-trans-1'-nonenyl)-3α-hyroxy-7-(2'-(N-benzylphenylcarbamoylmethoxy)ethyl)-cis-bicyclo[3,3,0]octane.

NMR δ (CDCl₃) 3.85 (2H, s), 4.0 (1H, m) 4.90 (2H, s), 5.49 (2H, m).

2β-(3'β-hydroxy-4'-methyl-trans-1'-pentenyl)-3α-hydroxy-7-(2'-(N-benzylphenylcarbamoylmethoxy)ethyl)-cis-bicyclo[3,3,0]octane.

NMR δ (CDCl₃) 3.82 (2H, s), 4.88 (2H, s), 5.55 (2H, m).

2β-(3'α-hydroxy-4'-methyl-trans-1'-pentenyl)-3α-hydroxy-7-(2'-(N-benzylphenylcarbomoylmethoxy)ethyl)-cis-bicyclo[3,3,0]octane.

NMR δ (CDCl₃) 3.83 (2H, s), 4.88 (2H, s) 5.47 (2H, m).

2β-(3'β-hydroxy-5'-methyl-trans-1'-hexenyl)-3α-hydroxy-7-(2'-(N-benzylphenylcarbamoylmethoxy)ethyl)-cis-bicyclo[3,3,0]octane.

NMR δ (CDCl₃) 0.91 (6H, d, J=7 Hz), 3.84 (2H, s) 4.88 (2H, s), 5.59 (2H, m).

2β-(3'α-hydroxy-5'-methyl-trans-1'-hexenyl-3α-hydroxy-7-(2'-(N-benzylphenylcarbamoylmethoxy)ethyl)-cis-bicyclo[3,3,0]octane.

NMR δ (CDCl₃) 0.91 (6H, d, J=7 Hz, 3.82 (2H, s) 4.88 (2H, s), 5.49 (2H, m).

2β-(3'β-hydroxy-5'-methyl-trans-1'-nonenyl)-3α-hydroxy-7-(2'-(N-benzylphenylcarbamoylmethoxy)ethyl)-cis-bicyclo[3,3,0]octane.

NMR δ (CDCl₃) 3.67 (1H, m), 3.83 (2H, s), 4.13 (1H, m) 4.85 (2H, s), 5.57 (2H, m).

2β-(3'α-hydroxy-5'-methyl-trans-1'-nonenyl)-3α-hydroxy-7-(2'-(N-benzylphenylcarbamoylmethoxy)ethyl)-cis-bicyclo[3,3,0]octane.

NMR δ (CDCl₃) 3.63 (1H, m), 3.82 (2H, s), 4.10 (1H, m) 4.86 (2H, s), 5.46 (2H, m).

2β-(3'β-hydroxy-4'-ethyl-trans-1'-octenyl)-3α-hydroxy-7-(2'-(N-benzylphenylcarbamoylmethoxy)ethyl)-cis-bicyclo[3,3,0]octane.

NMR δ (CDCl₃) 3.81 (2H, s), 4.87 (2H, s), 5.53 (2H, m).

2β-(3'α-hydroxy-4'-ethyl-trans-1'-octenyl)-3α-hydroxy-7-(2'-(N-benzylphenylcarbamoylmethoxy)ethyl)-cis-bicyclo[3,3,0]octane.

NMR δ (CDCl₃) 3.81 (2H, s), 4.86 (2H, s), 5.50 (2H, m).

2β-(3'-hydroxy-4',4'-dimethyl-trans-1'-octenyl)-3α-hydroxy-7-(2'-(N-benzylphenylcarbamoylmethoxy)ethyl)-cis-bicyclo[3,3,0]octane.

NMR δ (CDCl₃) 0.90 (9H, m), 3.81 (2H, s) 4.89 (2H, s), 5.58 (2H, m).

2β-(3'-hydroxy-4'-methylene-trans-1'-octenyl)-3α-hydroxy-7-(2'-(N-benzylphenylcarbamoylmethoxy)ethyl)-cis-bicyclo[3,3,0]octane.

NMR δ (CDCl₃) 3.83 (2H, s), 4.10 (1H, m), 4.89 (2H, s) 5.01 (1H, s), 5.10 (1H, s), 5.58 (2H, m).

2β-(3'β-hydroxy-5',9'-dimethyl-trans-1',8'-decadienyl)-3α-hydroxy-7-(2'-(N-benzylphenylcarbamoylmethoxy)ethyl)-cis-bicyclo[3,3,0]octane.

NMR δ (CDCl₃) 1.60 (3H, s), 1.65 (3H, s) 3.82 (2H, s), 4.88 (2H, s), 5.56 (2H, m).

2β-(3'α-hydroxy-5',9'-dimethyl-trans-1',8'-decadienyl)-3α-hydroxy-7-(2'-(N-benzylphenylcarbamoylmethoxy)ethyl)-cis-bicyclo[3,3,0]octane.

NMR δ (CDCl₃) 1.60 (3H, s), 1.65 (3H, s) 3.81 (2H, s), 4.88 (2H, s), 5.46 (2H, m).

2β-(3'β-hydroxy-4'-methyl-trans-1'-octen-6'-ynyl)-3α-hydroxy-7-(2'-(N-benzylphenylcarbamoylmethoxy)ethyl)-cis-bicyclo[3,3,0]octane.

NMR δ (CDCl₃) 3.83 (2H, s), 3.98 (1H, m) 4.89 (2H, s), 5.57 (2H, m).

2β-(3α-hydroxy-4'-methyl-trans-1'-octen-6'-ynyl)-3α-hydroxy-7-(2'-(N-benzylphenylcarbamoylmethoxy)ethyl)-cis-bicyclo[3,3,0]octane.
NMR δ (CDCl₃) 3.83 (2H, s), 3.98 (1H, m) 4.88 (2H, s), 5.53 (2H, m).

2β-(3'β-hydroxy-3'-cyclopentyl-trans-1'-propenyl)-3-hydroxy-7-(2'-(N-benzylphenylcarbamoylmethoxy)ethyl)-cis-bicyclo[3,3,0]octane.
NMR δ (CDCl₃) 3.83 (2H, s), 4.87 (2H, s), 5.56 (2H, m).

2β-(3'α-hydroxy-3'-cyclopentyl-trans-1'-propenyl)-3α-hydroxy-7-(2'-(N-benzylphenylcarbamoylmethoxy)ethyl)-cis-bicyclo[3,3,0]octane.
NMR δ (CDCl₃) 3.82 (2H, s), 4.87 (2H, s), 5.50 (2H, m).

2β-(3'β-hydroxy-3'-cyclohexyl-trans-1'-propenyl)-3α-hydroxy-7-(2'-(N-benzylphenylcarbamoylmethoxy)ethyl)-cis-bicyclo[3,3,0]octane.
NMR δ (CDCl₃) 3.83 (2H, s), 4.90 (2H, s), 5.60 (2H, m).

2β-(3'α-hydroxy-3'-cyclohexyl-trans-1'-propenyl)-3α-hydroxy-7-(2'-(N-benzylphenylcarbamoylmethoxy)ethyl)-cis-bicyclo[3,3,0]octane.
NMR δ (CDCl₃) 3.83 (2H, s), 4.90 (2H, s), 5.48 (2H, m).

2β-(3'-hydroxy-3'-cyclohexyl-trans-1'-propenyl)-3α-hydroxy-7-(2'-dibenzylcarbamoylmethoxyethyl)-ci-bicyclo[3,3,0]octane.
NMR δ (CDCl₃) 4.03 (2H, s), 4.44 (4H, br), 5.36 (2H, m).

2β-(3'-hydroxy-3'-(2''-isopropylidenemethyl-3'',3''-dimethylcyclopropyl)-trans-1'-propenyl)-3α-hydroxy-7-(2'-(N-benzylphenylcarbamoylmethoxy)ethyl)-cis-bicyclo-[3,3,0]octane.
NMR δ (CDCl₃) 0.64 (1H, m), 3.83 (2H, s) 4.88 (2H, s), 5.57 (2H, m).

2β-(3'β-hydroxy-3'-(cyclohexen-4'-yl)-trans-1'-propenyl)-3α-hydroxy-7-(2'-(N-benzylphenylcarbamoylmethoxy)ethyl)-cis-bicyclo[3,3,0]octane.
NMR δ (CDCl₃) 3.83 (2H, s), 4.90 (2H, s) 5.59 (2H, m), 5.68 (2H, s).

2β-(3'α-hydroxy-3'-(cyclohexen-4''-yl)-trans-1'-propenyl)-3α-hydroxy-7-(2'-(N-benzylphenylcarbamoylmethoxy)ethyl)-cis-bicyclo[3,3,0]octane.
NMR δ (CDCl₃) 3.83 (2H, s), 4.89 (2H, s) 5.50 (2H, m), 5.67 (2H, s).

2β-(3β-hydroxy-3'-(bicyclo[4,3,0]nona-3''-en-8''-yl)-trans-1'-propenyl)-3α-hydroxy-7-(2'-(N-benxylphenylcarbamoylmethoxy)ethyl)-cis-bicyclo[3,3,-0]octane.
NMR δ (CDCl₃) 3.81 (2H, s), 4.88 (2H, s), 5.60 (4H, br).

2β-(3'α-hydroxy-3'-(bicyclo[4,3,0]nona-3''-en-8''-yl)-trans-1'-propenyl)-3α-hydroxy-7-(2'-(N-benzylphenylcarbamoylmethoxy)ethyl)-cis-bicyclo[3,3,-0]octane.
NMR δ (CDCl₃) 3.82 (2H, s), 4.87 (2H, s) 5.48 (2H, m), 5.60 (2H, brs).

2β-(3β-hydroxy-3'-(4''-fluorophenyl)-trans-1'-propenyl)-3α-hydroxy-7-(2'-(N-benzylphenylcarbamoylmethoxy)ethyl)-cis-bicyclo[3,3,0]octane.
NMR δ (CDCl₃) 3.80 (2H, s), 4.83 (2H, s), 5.12 (1H, m), 5.68 (1H, m).

2β-(3'α-hydroxy-3'-(4''-fluorophenyl)-trans-1'-propenyl)-3α-hydroxy-7-(2'-(N-benzylphenylcarbamoylmethoxy)ethyl)-cis-bicyclo[3,3,0]octane.
NMR δ (CDCl₃) 3.78 (2H, s), 4.82 (2H, s) 5.09 (1H, m), 5.63 (1H, m).

2β-(3'-hydroxy-4'-(1'''-adamantyl)-trans-1'-butenyl)-3α-hydroxy-7-(2'-(N-benzylphenylcarbamoylmethoxy)ethyl)-cis-bicycle[3,3,0]octane.
NMRδ (CDCl₃) 3.80 (2H, s), 4.86 (2H, s), 5.55 (2H, m).

2β-(3'α-hydroxy-4'-(bicyclo[4,3,0]nona-3''-ene-8''-yl)-trans-1'-butenyl)-3α-hydroxy-7-(2'-(N-benzylphenylcarbamoylmethoxy)ethyl)-cis-bicyclo[3,3,0]octane.
NMRδ (CDCl₃) 3.42 (2H, t, J=7 Hz), 3.82 (2H, s) 4.87 (2H, s), 5.48 (2H, m), 5.65 (2H, brs).

2β(3'-hydroxy-4'-(1-menthoxy)-trans-1'-butenyl)-3α-hydroxy-7-(2'-(N-benzylphenylcarbamoylmethoxy)ethyl)-cis-bicyclo[3,3,0]octane.
NRMδ (CDCl₃) 3.80 (2H, s), 4.89 (2H, s), 5.55 (2H, m).

2β-(3'β-hydroxy-4'-phenoxy-trans-1'-butenyl)-3α-hydroxyl-7-(2'-(N-benzylphenylcarbamoylmethoxy)ethyl)cis-bicyclo[3,3,0]octane.
NMRδ (CDCl₃) 3.82 (2H, s), 4.48 (1H, m) 4.88 (2H, s), 5.69 (2H, m).

2β-3'α-hydroxy-4'-phenoxy-trans-1'-butenyl)-3α-hydroxyl-7-(2'-(N-benzylphenylcarbamoylmethoxy)ethyl)cis-bicyclo[3,3,0]octane.
NMRδ (CDCl₃) 3.83 (2H, s), 4.45 (1H, m) 4.88 (2H, s), 5.64 (2H, m).

2β-(3'-hydroxy-4'-(4''-fluorophenoxy)-trans-1'-butenyl)-3α-(tetrahydropyran-2'-yloxy)-7-(2'-(diethylcarbamoylmethoxy)ethyl)-cis-bicyclo[3,3,0]octane.
NMRδ (CDCl₃) 4.10 (2H, s), 4.49 (1H, m) 4.62 (1H, m), 5.72 (2H, m).

2β-(3'β-hydroxy-4'-(4''-fluorophenoxy)-trans-1'-butenyl)-3α-hydroxy-7-(2'-diethylcarbamoylmethoxy)ethyl)cis-bicyclo[3,3,0]octane.
NMRδ (CDCl₃) 4.10 (2H, s), 4.48 (1H, m), 5.68 (2H, m).

2β-(3'α-hydroxy-4'-(4''-fluorophenoxy)-trans-1'-butenyl)-3α-hydroxy-7-(2'-diethylcarbamoylmethoxy)ethyl)cis-bicyclo[3,3,0]octane.
NMRδ (CDCl₃) 4.10 (2H, s), 4.41 (1H, m), 5.60 (2H, m).

2β-(3'-hydroxy-5'-ethoxy-trans-1'-pentenyl)-7-(2'-(N-benzylphenylcarbamoylmethoxy)ethyl)-cis-bicyclo[3,3,0]oct-2-ene.
NMRδ (CDCl₃) 1.18 (3H, t, J=7 Hz), 3.80 (2H, s) 4.88 (2H, s), 5.56 (2H, m), 6.32 (1H, d, J=16 Hz).

2β-(2'-bromo-3'-hydroxy-3'-cyclopentyl-trans-1'-propenyl)-3'α-hydroxy-7-(2'-(N-benzylphenylcarbamoylmethoxy)ethyl)-cis-bicyclo[3,3,0]octane.
NMRδ (CDCl₃) 3.81 (2H, s), 4.88 (2H, s) 5.83 (1H, d, J=8 Hz).

2β-(2'-bromo-3'β-hydroxy-4'-methyl-trans-1'-pentenyl)-3α-hydroxy-7-(2'-(N-benzylphenylcarbamoylmethoxy)ethyl)-cis-bicyclo[3,3,0]octane.
NMRδ (CDCl₃) 3.83 (2H, s), 4.86 (2H, s) 5.87 (1H, d, J=9 Hz).

2β-(2'-bromo-3'α-hydroxy-4'-methyl-trans-1'-pentenyl)-3α-hydroxy-7-(2'-(N-benzylphenylcarbamoylmethoxy)ethyl)-cis-bicyclo[3,3,0]octane.
NMRδ (CDCl₃) 3.82 (2H, s), 4.89 (2H, s) 5.78 (1H, d, J=9 Hz).

2β(2'-bromo-3'-hydroxy-5'-methyl-trans-1'-nonenyl)-3α-hydroxy-7-(2'-(N-benzylphenylcarbamoylmethoxy)ethyl)-cis-bicyclo[3,3,0]octane.
NMRδ (CDCl₃) 3.82 (2H, s), 4.87 (2H, s) 5.81 (1H, d, J=9 Hz).

2β-(2'-bromo-3'-hydroxy-5',9'-dimethyl-trans-1',8'-decadienyl)-3α-hydroxy-7-(2'-(N-benzylphenylcarbamoylmethoxy)ethyl)-cis-bicyclo[3,3,0]octane.

NMRδ (CDCl$_3$) 3.82 (2H, s), 4.88 (2H, s) 5.80 (1H, d, J=8 Hz).

2β-(2'-bromo-3'-hydroxy-4'-methyl-trans-1'-octen-6'-ynyl)-3α-hydroxy-7-(2'-(N-benzylphenylcarbamoylmethoxy)ethyl)-cis-bicyclo[3,3,0]octane.

NMRδ (CDCl$_3$) 3.82 (2H, s), 5.82 (1H, d, J=9 Hz).

EXAMPLE 5

Into a THF solution (20 ml) of 2β-(3'-oxo-5',9'-dimethyl-trans-1',8'-decadienyl)-3α-hydroxy-7-(2'-N-benzylphenylcarbamoylmethoxyethyl)-cis-bicyclo[3,3-0]octane (1.8 g) was added a solution of methylmagnesium iodide prepared from magnesium ribbon (0.48 g) and methyliodide (2.8 g) in dry ether (25 ml). After being stirred at 5° C. for 0.5 hr and then at room temperature for one hour, the mixture was poured into saturated ammonium chloride solution and extracted with ethyl acetate. The organic layer was washed with brine, dried and concentrated in vacuo.

The residue was chromatographed on silica gel to give 2β-(3'-hydroxy-3',5',9'-trimethyl-trans-1',8'-decadienyl)-3α-hydroxy-7-(2'-(N-benzylphenylcarbamoylmethoxyethyl)-cis-bicyclo[3,3,0]octane.

NMRδ (CDCl$_3$) 1.25 (3H, s), 1.60 (3H, s), 1.65 (3H, s) 3.82 (2H, s), 4.88 (2H, s), 5.50 (2H, m).

EXAMPLE 6

To a tert-butanol solution (15 ml) of 2β-(2β-2'-bromo-3'-hydroxy-3'-cyclopentyl-trans-1'-propenyl)-3α-hydroxy-7-(2'-(N-benzylphenylcarbamoyl methoxy)ethyl)cis-bicyclo[3,3,0]octane (310 mg), was added potassium tert-butoxide (100 mg), and the mixture was stirred at room temperature for 5 hr. The mixture was poured into water and extracted with ethyl acetate. The extract was washed with water, dried, concentrated, and then chromatographed to give 2β-(3'-hydroxy-3'-cyclopentyl-1'-propynyl)-3α-hydroxy-7-(2'-(N-benzylphenylcarbamoyl methoxy)ethyl)-cis-bicyclo[3,3,0]octane.

NMRδ (CDCl$_3$) 3.81 (2H, 3), 4.88 (2H, s) 6.93–7.04 (2H, m), 7.23–7.34 (8H, m).

EXAMPLE 7

According to the same procedure as Example 5, there were obtained the following compounds.

2β-(3'α-hydroxy-4'-methyl-1'-pentynyl)-3α-hydroxy-7-(2'-(N-benzylphenylcarbamoylmethoxy)ethyl)-cis-bicyclo-[3,3,0]octane.

NMRδ (CDCl$_3$) 3.82 (2H, δ), 4.88 (2H, s) 6.92–7.05 (2H, m), 7.23–7.35 (8H, m).

2β(3'-hydroxy-5'-methyl-1'-nonynyl)-3α-hydroxy-7-(2'-(N-benzylphenylcarbamoylmethoxy)ethyl)cis-bicyclo[3,3,0]octane.

NMRδ (CDCl$_3$) 3.82 (2H, s), 4.86 (2H, s) 6.92–7.03 (2H, m), 7.23–7.35(8H, m).

2β-(3'-hydroxy-5',9'-dimethyl-8'-decene-1'-ynyl)-b 3α-hydroxy-7-(2'-(N-benzylphenylcarbamoylmethoxy)ethyl)-cis-bicyclo[3,3,0]octane.

NMRδ (CDCl$_3$) 1.60 (3H, s), 1.65 (3H, s).

2β-(3'-hydroxy-4'-methyl-1',6'-octdiynyl)-3α-hydroxy-7-(2'-(N-benzylphenylcarbamoylmethoxy)ethyl)-cis-bicyclo[ 3,3,0]octane.

NMRδ (CDCl$_3$) 3.83 (2H, s), 6.93–7.04 (2H, m) 7.23–7.35 (8H, m).

EXAMPLE 8

A mixture of 2β-(3'α-hydroxy-trans-1'-octenyl)-3α-hydroxy-7-(2'-(N-benzylphenylcarbamoylmethoxy)ethyl)cis-bicyclo[3,3,0]octane (1.5 g), potassium hydroxide (1.5 g), water (15 g), ethanol (12 g) was refluxed for 7 hr. After-cooling, the mixture was poured into water and extracted with diethyl ether. The aqueous layer was acidified with aqueous solution of potassium hydrogen sulfate and extracted with ethyl acetate. The ethyl acetate layer was washed with water, dried and concentrated at reduced pressure to give 2β-(3'α-hydroxy-trans-1'-octenyl)-3α-hydroxy-7-(2'-carboxymethoxyethyl)-cisbicyclo[3,3,0]octane as an oil NMR δ (CDCl$_3$) 3.58 (3H, m), 4.0 (1H, m) 4.08 (2H, s), 5.52 (5H, br).

EXAMPLE 9

A mixture of 2β-(3'-hydroxy-3'-cyclohexyl-trans-1'-propenyl)-3α-hydroxy-7-(2'-dibenzylcarbamoylmethoxyethyl)-cis-bicyclo[3,3,0]octane (0.4 g), potassium hydroxide (0.8 g), water (5 g) and ethylene glycol (7 g) was stirred under reflux for 10 hr. After cooling, the mixture was poured into water and extracted with diethyl ether. The aqueous layer was acidified with aqueous solution of potassium hydrogen sulfate and extracted with ethyl acetate. The organic layer was washed with water, dried and concentrated to give 2β-(3'hydroxy-3'-cyclohexyl-trans-1'-propexyl)-3α-hydroxy(2'-carboxymethoxyethyl)-cis-bicyclo[3,3,0]octane.

NMR δ (CDCl$_3$) 4.07 (2H, s), 4.20 (3H, br), 5.48 (2H, m).

EXAMPLE 10

According to the same procedures as example 7, or Example 8, there were obtained the following compounds.

2β-(3'β-hydroxy-trans-1'-octenyl)-3α-hydroxy-7-(2'-carboxymethoxyethyl)-cis-bicyclo[3,3,0]octane.

NMRδ (CDCl$_3$) 5.09 (3H, brd), 5.50 (2H, m).

2β-(3'β-hydroxy-trans-1'-nonenyl)-3α-hydroxy-7-(2'-carboxymethoxyethyl)-cis-bicyclo[3,3,0]octane.

NMRδ (CDCl$_3$) 0.88 (3H, t-like), 4.08 (3H, br), 5.60 (2H, m), 5.90 (3H, br).

2β-(3'α-hydroxy-trans-1'-nonenyl)-3α-hydroxy-7-(2'-carboxymethoxyethyl)-cis-bicyclo[3,3,0]octane.

NMRδ (CDCl$_3$) 0.88 (3H, t-like), 4.08 3H, br), 5.50 (5H, br).

2β-(3'8-hydroxy-4'-methyl-trans-1'-pentenyl)-3α-hydroxy-7-(2'-carboxymethoxyethyl)-cis-bicyclo[3,3,0]octane.

NMRδ (CDCl$_3$) 0.90 (6H, m), 4.09 (2H, s), 5.68 (5H, br).

2β(3'αhydroxy-4'-methyl-trans-1'-pentenyl-3α-hydroxy-7-(2'-carboxymethoxyethyl)-cis-bicyclo[3,3,-0]octane.

NMRδ (CDCl$_3$) 0.90 (6H, m), 4.08 (2H, s) 5.56 (5H, br).

2β-(3β-hydroxy-5'-methyl-trans-1'-hexenyl)-3α-hydroxy-7-(2'-carboxymethoxyethyl)-cis-bicyclo[3,3,0]octane.

NMRδ (CDCl$_3$) 0.90 (6H, d, J=7 Hz), 4.04 (3H, br), 5.53 (5H, br).

2β(3'α-hydroxy-5'-methyl-trans-1'-hexenyl)-3α-hydroxy-7-(2'-carboxymethoxyethyl)-cis-bicyclo[3,3,0]-octane.

NMRδ (CDCl₃) 0.90 (6H, d, J=7 Hz), 4.03 (3H, br), 5.43 (2H, m), 6.03 (3H, br).

2β-(3'β-hydroxy-5'-methyl-trans-1'-nonenyl)-3α-hydroxy-7-(2'-carboxymethoxyethyl)-cis-bicyclo[3,3,0]-octane.

NMRδ (CDCl₃) 4.08 (2H, s), 4.98 (3H, br), 5.59 (2H, m).

2β-(3'α-hydroxy-5'-methyl-trans-1'-nonenyl)-3α-hydroxy-7-(2'-carboxymethoxyethyl)-cis-bicyclo[3,3,0]-octane.

NMRδ (CDCl₃) 4.05 (2H, s), 4.72 (3H, br), 5.46 (2H, m).

2β-(3'β-hydroxy-4'-ethyl-trans-1'-octenyl)-3α-hydroxy-7-(2'-carboxymethoxyethyl)-cis-bicyclo[3,3,0]-octane.

NMRδ (CDCl₃) 0.90 (6H, br), 4.09 (2H, s), 5.60 (2H, m), 5.76 (3H, br).

2β-(3'α-hydroxy-4'-ethyl-trans-1'-octenyl)-3α-hydroxy-7-(2'-carboxymethoxyethyl)-cis-bicyclo[3,3,0]-octane.

NMRδ (CDCl₃) 0.90 (6H, br), 4.10 (2H, s), 5.53 (5H, br).

2β-(3'-hydroxy-4',4'-dimethyl-trans-1'-octenyl)-3α-hydroxy-7-(2'-carboxymethoxyethyl)-cis-bicyclo[3,3,0]-octane.

NMRδ (CDCl₃) 0.88 (9H, m), 4.09 (2H, s), 5.72 (5H, br).

2β-(3'-hydroxy-4'-methylene-trans-1'-octenyl)-3α-hydroxy-7-(2'-carboxymethoxyethyl)-cis-bicyclo[3,3,0]-octane.

NMRδ (CDCl₃) 4.87 (3H, br), 5.02 (1H, s), 5.10 (1H, br), 5.60 (2H, m). 2β-(3'8-hydroxy-5',9'-dimethyl-trans-1',8'-decadienyl)-3α-hydroxy-7-(2'-carboxymethoxyethyl)-cisbicyclo[3,3,0]octane.

NMRδ (CDCl₃) 1.61 (3H, s), 1,68 (3H, s), 4.08 (2H, s), 5.10 (1H, t, J=7 Hz), 5.35 (3H, br), 5.58 (2H, m).

2β-(3'α-hydroxy-5',9'-dimethyl-trans-1',8'-decadienyl)-3α-hydroxy-7-(2'-carboxymethoxyethyl)-cisbicyclo[3,3,0]octane.

NMRδ (CDCl₃) 1.61 (3H, s), 1.68 (3H, s), 4.10 (2H, s), 5.10 (1H, t, J=7 Hz), 5.60 (5H, brd). 2β-(3'β-hydroxy-4'-methyl-trans-1'-octen-6'-ynyl)3α-hydroxy-7-(2'-carboxymethoxyethyl)-cis-bicyclo[3,3,0]octane.

NMRδ (CDCl₃) 4.08 (2H, s), 4.32 (3H, br) 5.56 (2H, m). 2β-(3'α-hydroxy-4'-methyl-trans-1'-octen-6'-ynyl)-3α-hydroxy-7-(2'-carboxymethoxyethyl)-cis-bicyclo[3,3,0]octane.

NMRδ (CDCl₃) 4.09 (2H, s), 5.05 (3H, br), 5.55 (2H, m).

2β(3'8-hydroxy-3'-cyclopentyl-trans-1'-propenyl)-3α-hydroxy-7-(2'-carboxymethoxyethyl)-cisbicyclo[3,3,0]octane.

NMRδ (CDCl₃) 4.08 (2H, s), 5.30 (3H, br), 5.56 (2H, m).

2β-(3'α-hydroxy-3'-cyclopentyl-trans-1'-propenyl)-3α-hydroxy-7-(2'-carboxymethoxyethyl)-cisbicyclo[3,3,0]octane.

NMRδ (CDCl₃) 4.08.(2H, s), 5.39 (3H, br) , 5.49 (2H, m).

2β-(3'β-hydroxy-3'-cyclohexyl-trans-1'-propenyl)-3α-hydroxy-7-(2'-carboxymethoxyethyl)-cisbicyclo[3,3,0]octane.

NMRδ (CDCl₃) 4.08 (2H, s), 5.38 (3H, br), 5.56 (2H, m). 2β-(3'β-hydroxy-3'-cyclohexyl-trans-1'-propenyl)-3α-hydroxy-7-(2'-carboxymethoxyethyl)-cisbicyclo[3,3,0]octane.

NMRδ (CDCl₃) 4.07 (2H, s), 5.52 (5H, br).

2β-(3'-hydroxy-3'-(2"-isopropylidenemethyl-3",3"-dimethylcyclopropyl)- trans-1'-propenyl)-3α-hydroxy-7-(2'-carboxymethoxyethyl)-cis-bicyclo[3,3,0]-octane.

NMRδ (CDCl₃) 0.63 (1H, m), 4.08 (2H, s), 4.43 (3H, br), 5.53 (2H, m).

2β-(3'β-hydroxy-3'-(cyclohexene-4"-yl)-trans-1'-propenyl)-3α-hydroxy-7-(2'-carboxymethoxyethyl)-cisbicyclo[3,3,0]octane.

NMRδ (CDCl₃) 4.03 (2H, s), 5.48 (5H, br), 5.58 (2H, brs).

2β(3'α-hydroxy-3'-(cyclohexene-4"-yl)-trans-1'-propenyl)-3α-hydroxy-7-(2'-carboxymethoxyethyl)-cisbicyclo[3,3,0]octane.

NMRδ (CDCl₃) 4.03 (2H, s), 5.37 (5H, br), 5.57 (2H, brs).

2β-(3'β-hydroxy-3'-(bicyclo[4,3,0]nona-3"-en-8"-yl)-transl'-propenyl)-3α-hydroxy-7-(2'-carboxymethoxyethyl)-cis-bicyclo[3,3,0]octane.

NMRδ (CDCl₃) 4.06 (2H, s), 5.61 (7H, br),

2β-(3'α-hydroxy-3'-(bicyclo[4,3,0]nona-3"-en-8"-yl)-trans-1'-propenyl)-3α-hydroxy-7-(2'-carboxymethoxyethyl)-cis-bicyclo[3,3,0]octane.

NMRδ (CDCl₃) 4.07 (2H, s), 5.45 (5H, br), 5.67 (2H, brs).

2β-(3'β-hydroxy-3'-(4"-fluorophenyl)-trans-1'-propenyl)- 3α-hydroxy-7-(2'-carboxymethoxyethyl)-cisbicyclo[3,3,0]octane.

NMRδ (CDCl₃) 4.02 (2H, s), 4.10 (1H, m), 5.63 (2H, m), 6.14 (3H, br), 6.85–7.10 (4H, m).

2β-(3'α-hydroxy-3'-(4"-fluorophenyl)-trans-1'-propenyl)-3α-hydroxy-7-(2'-carboxymethoxyethyl)-cisbicyclo[3,3,0]octane.

NMRδ (CDCl₃) 3.90 (3H, br), 4.07 (2H, s), 4.10 (1H, m), 5.67 (2H, m), 6.90–7.45 (4H, m).

2β-(3'-hydroxy-4'-(1'''-adamantyl)-trans-1'-butenyl)-3α-hydroxy-7-(2'-carboxymethoxyethyl)-cisbicyclo[3,3,0]octane.

NMRδ (CDCl₃) 4.08 (2H, s), 5.00 (3H, br) 5.53 (2H, m).

2β-(3'α-hydroxy-4'-(bicyclo[4,3,0]nona-3"-en-8"-yl)-trans-1'-butenyl)-3α-hydroxy-7-(2'-carboxymethoxyethyl)-cis bicyclo[3,3,0]octane.

NMRδ (CDCl₃) 4.07 (2H, s), 5.48 (2H, m), 5.67 (2H, brs), 5.78 (3H, br).

2β-(3'-hydroxy-4'-(l-menthoxy)-trans-1'-butenyl)-3α-hydroxy-7-(2'-carboxymethoxyethyl)-cisbicyclo[3,3,0]octane.

NMRδ (CDCl₃) 4.10 (2H, s), 5.62 (2H, m), 6.48 (3H, br).

2β-(3'β-hydroxy-4'-phenoxy-trans-1'-butenyl)-3-hydroxy-7-(2'-carboxymethoxyethyl)-cis-bicyclo[3,3,0]-octane.

NMRδ (CDCl₃) 4.03 (2H, s), 4.45 (1H, m), 5.65 (2H, m), 5.8 (3H, br), 6.8–7.35 (5H, m).

2β-(3'α-hydroxy-4'-phenoxy-trans-1'-butenyl)-3α-hydroxy-7-(2'-carboxymethoxyethyl)-cis-bicyclo[3,3,0]-octane.

NMRδ (CDCl₃) 4.03 (2H, s), 4.43 (1H, m), 5.60 (2H, m), 5.82 (3H, br), 6.80–7.32 (5H, m).

2β-(3'-hydroxy-3'-cyclopentyl-1'-propynyl)-3α-hydroxy-7-(2'-carboxymethoxyethyl)-cis-bicyclo-[3,3,0]-octane.

NMR δ (CDCl₃) 4.10 (2H, s), 4.22 (1H, m), 5.70 (3H, br).

2β-(3'-hydroxy-5'-methyl-1'-nonynyl)-3α-hydroxy-7-(2'-carboxymethoxyethyl)-cis-bicyclo[3,3,0]-octane.

NMRδ (CDCl₃) 4.09 (2H, s), 5.80 (3H, br).

2β-(3'-hydroxy-5',9'-dimethyl-8'-decene-1'-ynyl)-3α-hydroxy-7-(2'-carboxymethoxyethyl)-cis-bicyclo-[3,3,0]-octane.

NMRδ (CDCl3) 4.09 (2H, s), 5.10 (1H, t, J=7 Hz) 5.60 (3H, brd).

2β-(3'-hydroxy-4'-methyl-1',6'-octdiynyl)-3α-hydroxy-7-(2'-carboxymethoxyethyl)-cis-bicyclo-[3,3,0]octane.

NMRδ (CDCl3) 4.08 (2H, s), 5.60 (3H, br).

2β-(3'-hydroxy-3',5',9'-trimethyl-trans-1',8'-decadienyl)-3α-hydroxy-7-(2'-carboxymethoxyethyl)-cisbicyclo[3,3,0]octane.

NMRδ (CDCl3) 1.25 (3H, s), 4.09 (2H, s), 5.10 (1H, t, J=7 Hz), 5.60 (5H, brd).

EXAMPLE 11

A mixture of 2β-(3'α-hydroxy-5'-methyl-trans-1'-nonenyl)-3α-hydroxy-7-(2'-carboxymethoxyethyl)-cis-bicyclo[3,3,0]octane (100 mg), 10% Palladium on charcoal (64 mg) and methanol (20 ml) was stirred under an atmosphere of hydrogen at room temperature. The mixture was filtered and washed with methanol. The filtrate was condensed under reduced pressure to give 2β-(3'α-hydroxy-5'-methylnonyl)-7-(2'-carboxymethoxyethyl)-cis-bicyclo[3,3,0]octane.

NMRδ (CDCl3) 0.9 (6H, m), 4.10 (2H, s), 5.48 (3H, brd).

EXAMPLE 12

To a diethyl ether solution (30 ml) of 2β-(3'α-hydroxy-4'-methyl-trans-1'-octen-6'-ynyl)-3α-hydroxy-7-(2'-carboxymethoxyethyl)-cis-bicyclo[3,3,0]octane (100 mg), was added a diethyl ether solution (20 ml) of diazomethane, and then the mixture was left at room temperature for 10 hr. The mixture was concentrated and chromatographed to give 2β-(3'α-hydroxy-4'-methyltrans-1'-octen-6'-ynyl)-3α-hydroxy-7-(2'-methoxycarbonylmethoxyethyl)-cis-bicyclo[3,3,0]octane.

NMRδ (CDCl3) 2.80 (2H, br), 3.77 (3H, s).

EXAMPLE 13

A methanol solution (20 ml) of 2β-(3'α-hydroxy-4'-methyl-trans-1'-octen-6'-ynyl)-3α-hydroxy-7-(2'-methoxycarbonylmethoxyethyl)-cis-bicycle [3,3,0]octane (50 mg), was added to a methanol solution (100 ml) of ammonia, and then the mixture was left at room temperature. After the starting material was disappeared, the mixture was concentrated under reduced pressure to give 2β-(3'α-hydroxy-4'-methyl-trans-1'-octen-6'-ynyl)-3α- hydroxy-7-(2'-carbamoylmethoxyethyl)-cis-bicyclo[3,3,0] actane.

NMR (CDCl3) 2.83 (2H, br), 3.93 (2H, s), 5.50 (2H, m), 6.03 and 6.50 (2H, br).

What is claimed is:

1. A compound of the formula:

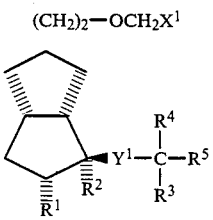

wherein $X^1$ is a free carboxyl group or an esterified carboxyl group selected from the group consisting of $C_1$–$C_4$ alkoxycarbonyl, phenoxycarbonyl, naphthoxycarbonyl, benzyloxycarbonyl, phenethyloxycarbonyl, ($C_1$–$C_4$ alkoxy)methoxycarbonyl, ($C_2$–$C_5$ alkanoyloxy)-methoxycarbonyl, ($C_3$–$C_7$ cycloalkyloxy)carbonyl, phenylcarbonylmethoxycarbonyl and (hydroxy $C_1$–$C_4$ alkoxy)carbonyl, $Y^1$ is a group of the formula:

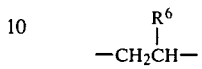

($R^6$ is a hydrogen atom or a $C_1$–$C_4$ alkyl group),

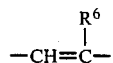

($R^6$ is as defined above),

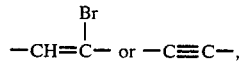

$R^1$ is a hydrogen atom, a hydroxyl group or a hydroxy group protected with $C_1$–$C_4$ alkanoyl, benzoyl, tetrahydropyranyl, tetrahydrofuryl or ($C_1$–$C_4$ alkoxy)methyl, $R^2$ is a hydrogen atom or $R^1$ and $R^2$, when taken together, mean a single linkage to form a double bond between the carbon atoms to which they are linked, $R^3$ is a hydroxyl group or a hydroxy group protected with $C_1$–$C_4$ alkanoyl, benzoyl, tetrahydropyranyl, tetrahydrofuryl or ($C_1$–$C_4$ alkoxy)methyl, $R^4$ is a hydrogen atom or a $C_1$–$C_4$ alkyl group, $R^5$ is a hydrogen atom, a $C_1$–$C_{12}$ alkyl group, a $C_2$–$C_{12}$ alkenyl group, a $C_2$–$C_{12}$ alkynyl group, a $C_3$–$C_{10}$ cycloalkyl group, a $C_4$–$C_{10}$ cycloalkenyl group, a hydroxy $C_1$–$C_{12}$ alkyl group, a phenyl group unsubstituted or substituted with a halogen atom, a hydroxyl group, a $C_1$–$C_4$ alkyl group, a trifluoromethyl group, or a $C_1$–$C_4$ alkoxy group or a group of the formula: A-B (A is a $C_1$–$C_7$ alkylene chain and B is a $C_3$–$C_{10}$ cycloalkyl group, a $C_4$–$C_{10}$ cycloalkenyl group, a $C_1$–$C_{12}$ alkoxy group, a $C_3$–$C_{10}$ cycloalkoxy group, a $C_4$–$C_{10}$ cycloalkenyloxy group, or a phenyl or phenoxy group unsubstituted or substituted with a halogen atom, a hydroxy group, a $C_1$–$C_4$ alkyl group, a trifluoromethyl group or a $C_1$–$C_4$ alkoxy group); or a non-toxic pharmaceutically acceptable salt thereof.

2. The compound according to claim 1, wherein $X^1$ is a free carboxyl group, or a $C_1$–$C_4$ alkoxycarbonyl group, $R^5$ is a $C_1$–$C_{12}$ alkyl group, a $C_2$–$C_{12}$ alkenyl group, a $C_2$–$C_{12}$ alkynyl group, a $C_3$–$C_{10}$ cycloalkyl group, a $C_4$–$C_{10}$ cycloalkenyl group, a phenyl group optionally substituted with a halogen atom or a groups of the formula: A-B (A is a methylene group or a ethylene group and B is a $C_3$–$C_{10}$ cycloalkyl group, a $C_4$–$C_{10}$ cycloalkenyl group, a $C_1$–$C_{12}$ alkoxy group, a $C_3$–$C_{10}$ cycloalkoxy group, or a phenoxy group optionally substituted with a halogen atom).

3. The compound of claim 1 which is represented by the formula:

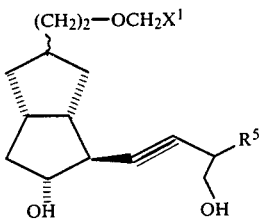

wherein $X^1$ and $R^5$ are each as defined in claim 1.

4. The compound of claim 1 which is represented by the formula:

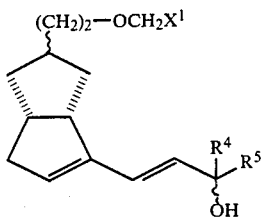

wherein $X^1$, $R^4$ and $R^5$ are each as defined in claim 1.

5. The compound of claim 1 which is represented by the formula:

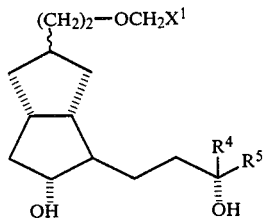

wherein $X^1$, $R^4$ and $R^5$ are each as defined in claim 1.

6. The compound of claim 1 which is represented by the formula:

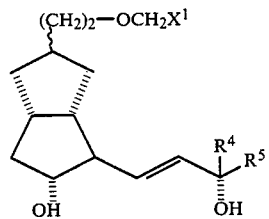

wherein $X^1$, $R^4$ and $R^5$ are each as defined in claim 1.

7. The compound according to claim 1, 3, 4, 5 or 6 wherein $X^1$ is a free carboxyl group or a $C_1$–$C_4$ alkoxycarbonyl group.

8. The compound according to claim 3, wherein $X^1$ is a free carboxyl group or a $C_1$–$C_4$ alkoxycarbonyl group, $R^5$ is a $C_1$–$C_{12}$ alkyl group, a $C_2$–$C_{12}$ alkenyl group, a $C_2$–$C_{12}$ alkynyl group, or a $C_3$–$C_{10}$ cycloalkyl group.

9. The compound according to claim 4, wherein $X^1$ is a free carboxyl group or a $C_1$–$C_4$ alkoxycarbonyl group, $R^4$ is a hydrogen atom, $R^5$ is a $C_1$–$C_{12}$ alkyl group, a $C_2$–$C_{12}$ alkenyl group, or a $C_1$–$C_{12}$ alkoxyethyl group.

10. The compound according to claim 5, wherein $X^1$ is a free carboxyl group or a $C_1$–$C_4$ alkoxycarbonyl group, $R^4$ is a hydrogen atom, $R^5$ is a $C_1$–$C_{12}$ alkyl group, or a $C_3$–$C_{10}$ cycloalkyl group.

11. The compound according to claim 6, wherein $X^1$ is a free carboxyl group or a $C_1$–$C_4$ alkoxycarbonyl group, $R^4$ is a hydrogen atom or a methyl group, $R^5$ is a $C_1$–$C_{12}$ alkyl group, a $C_2$–$C_{12}$ alkenyl group, a $C_2$–$C_{12}$ alkynyl group, a $C_3$–$C_{10}$ cycloalkyl group, a $C_4$–$C_{10}$ cycloalkenyl group, a phenyl group optionally substituted with a halogen atom or a group of the formula: A-B (A is a methylene group or an ethylene group and B is a $C_3$–$C_{10}$ cycloalkyl group, a $C_4$–$C_{10}$ cycloalkenyl group, a $C_1$–$C_{12}$ alkoxy group, a $C_3$–$C_{10}$ cycloalkoxy group, or a phenoxy group optionally substituted with a halogen atom).

12. 2β-(3'α-hydroxy-trans-1'-octenyl)-3α-hydroxy-7-(2'-carboxymethoxyethyl)-cis-bicyclo[3,3,0]octane, or its stereoisomer.

13. 2β-(3'α-hydroxy-trans-1'-nonenyl)-3α-hydroxy-7-(2'-carboxymethoxyethyl)-cis-bicyclo[3,3,0]octane, or its stereoisomer.

14. 2β-(3'α-hydroxy-4'-methyl-trans-1'-pentenyl)-3α-hydroxy-7-(2'-carboxymethoxyethyl)-cis-bicyclo[3,3,0]octane, or its stereoisomer.

15. 2β-(3'α-hydroxy-5'-methyl-trans-1'-hexenyl)-3α-hydroxy-7-(2'carboxymethoxyethyl)-cis-bicyclo[3,3,0]octane, or its stereoisomer.

16. 2β-(3'α-hydroxy-5'-methyl-trans-1'-nonenyl)-3α-hydroxy-7-(2'-carboxymethoxyethyl)-cis-bicyclo[3,3,0]octane, or its stereoisomer.

17. 2β-(3'α-hydroxy-4'-ethyl-trans-1'-octenyl)-3α-hydroxy-7-(2'-carboxymethoxyethyl)-cis-bicyclo[3,3,0]octane, or its stereoisomer.

18. 2β-(3'-hydroxy-4',4'-dimethyl-trans-1'-octenyl)-3α-hydroxy-7-(2'-carboxymethoxyethyl)-cis-bicyclo[3,3,0]octane.

19. 2β-(3'-hydroxy-4'-methylene-trans-1'-octenyl)-3α-hydroxy-7-(2'-carboxymethoxyethyl)-cis-bicyclo[3,3,0]octane.

20. 2β-(3'α-hydroxy-5',9'-dimethyl-trans-1',8'-decadienyl)-3α-hydroxy-7-(2'-carboxymethoxyethyl)-cisbicyclo[3,3,0]octane, or its stereoisomer.

21. 2β-(3'α-hydroxy-4'-methyl-trans-1'-octen-6'-ynyl)-3α-hydroxy-7-(2'-carboxymethoxyethyl)-cis-bicyclo[3,3,0]octane, or its stereoisomer.

22. 2β-(3'α-hydroxy-3'-cyclopentyl-trans-1'-propenyl)-3α-hydroxy-7-(2'-carboxymethoxyethyl)-cis-bicyclo[3,3,0]octane, or its stereoisomer.

23. 2β-(3'β-hydroxy-3'-cyclohexyl-trans-1'-propenyl)-3α-hydroxy-7-(2'-carboxymethoxyethyl)-cis-bicyclo[3,3,0]octane, or its stereoisomer.

24. 2β-(3'-hydroxy-3'-(2''-isopropylidenemethyl-3'',3''-dimethylcyclopropyl)-trans-1'-propenyl)-3α-hydroxy-7-(2'-carboxymethoxyethyl)-cis-bicyclo[3,3,0]octane.

25. 2β-(3'α-hydroxy-3'-(cyclohexen-4''-yl)-trans-1'-propenyl)-3α-hydroxy-7-(2'-carboxymethoxyethyl)-cis-bicyclo[3,3,0]octane, or its stereoisomer.

26. 2β-(3'α-hydroxy-3'-(bicyclo[4,3,0]nona-3'''-en-8''-yl)-trans-1'-propenyl)-3α-hydroxy-7-(2'-carboxymethoxyethyl)-cis-bicyclo[3,3,0]octane, or its stereoisomer.

27. 2β-(3'α-hydroxy-3'-(4''-fluorophenyl)-trans-1'-propenyl)-3α-hydroxy-7-(2'-carboxymethoxyethyl)-cis-bicyclo[3,3,0]octane, or its stereoisomer.

28. 2β-(3'-hydroxy-4'-(1'''-adamantyl)-trans-1'-butenyl)-3α-hydroxy-7-(2'-carboxymethoxyethyl)-cis-bicyclo[3,3,0]octane.

29. 2β-(3'-hydroxy-4'-(l-menthoxy)-trans-1'-butenyl)-3α-hydroxy-7-(2'-carboxymethoxyethyl-cis-bicyclo[3,3,0]octane.

30. 2β-(3'α-hydroxy-4'-phenoxy-trans-1'-butenyl)-3α-hydroxy-7-(2'-carboxymethoxyethyl)-cis-bicyclo[3,3,0]octane, and its stereoisomer.

31. 2β-(3'α-hydroxy-4'-(bicyclo[4,3,0]nona-3''-en-8''-yl)-trans-1'-butenyl)-3α-hydroxy-7-(2'-carboxymethoxyethyl)-cis-bicyclo[3,3,0]octane, or its stereoisomer.

32. 2β-(3'α-hydroxy-5'-methylnonyl)-7-(2'-carboxymethoxyethyl)-cis-bicyclo[3,3,0]octane, or its stereoisomer.

33. 2β-(3'α-hydroxy-3'-cyclopentylpropyl)-7-(2'-carboxymethoxyethyl)-cis-bicyclo[3,3,0]octane, or its stereoisomer.

34. 2β-(3'-hydroxy-3'-cyclopentyl-1'-propynyl)-3α-hydroxy-7-(2'-carboxymethoxyethyl)-cis-bicyclo[3,3,0]octane.

35. 2β-(3'α-hydroxy-4'-methyl-1'-pentynyl)-3α-hydroxy-7-(2'-carboxymethoxyethyl)-cis-bicyclo[3,3,0]octane, or its stereoisomer.

36. 2β-(3'α-hydroxy-4'-methyl-1',6'-octadiynyl)-3α-hydroxy-7-(2'-carboxymethoxyethyl)-cis-bicyclo[3,3,0]octane, or its stereoisomer.

37. 2β-(3'α-hydroxy-5',9'-dimethyl-8'-decen-1'-ynyl)-3α-hydroxy-7-(2'-carboxymethoxyethyl)-cis-bicyclo[3,3,0]octane, or its stereoisomer.

38. 2β-(3'α-hydroxy-4'-methyl-trans-1'-octen-6'-ynyl)-3α-hydroxy-7-(2'-methoxycarbonylmethoxyethyl)-cisbicyclo[3,3,0]octane, or its stereoisomer.

39. 2β-(3'α-hydroxy-5'-methyl-1'-nonynyl)-3α-hydroxy-7-(2'-carboxymethoxyethyl)-cis-bicyclo[3,3,0]-octane, or its stereoisomer.

40. 2β-(3'α-hydroxy-3',5',9'-trimethyl-trans-1',8'-decadienyl)-3α-hydroxy-7-(2'-carboxymethoxyethy)-cisbicyclo[3,3,0]octane.

41. The method of treating ulcers by administering to a patient an antiulcer effective amount of a compound as claimed in claim 1.

42. The method of treating thrombosis by administering to a patient an antithrombotic effective amount of a compound as claimed in claim 1.

43. A composition for the treatment of thrombosis or ulcers comprising a composition containing an antithrombic or anti-ulcerogenic effective amount of a compound as claimed in claim 1, and a pharmaceutically acceptable carrier or diluent.

* * * * *